US008012928B2

(12) United States Patent
Bluth et al.

(10) Patent No.: US 8,012,928 B2
(45) Date of Patent: Sep. 6, 2011

(54) TRUNCATED PAP2 AND METHODS OF MAKING AND USING SAME

(75) Inventors: Martin H. Bluth, Southfield, MI (US); Michael Zenilman, Lawrence, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 12/642,263

(22) Filed: Dec. 18, 2009

(65) Prior Publication Data
US 2010/0158809 A1    Jun. 24, 2010

Related U.S. Application Data

(60) Provisional application No. 61/138,984, filed on Dec. 19, 2008.

(51) Int. Cl.
*A61K 38/00* (2006.01)
*C12P 21/06* (2006.01)
*C07K 14/00* (2006.01)

(52) U.S. Cl. ......... 514/1.1; 435/69.1; 530/300; 530/350

(58) Field of Classification Search .................. None
See application file for complete search history.

(56) References Cited

U.S. PATENT DOCUMENTS

| | | | |
|---|---|---|---|
| 5,436,169 | A | 7/1995 | Iovanna et al. |
| 5,935,813 | A | 8/1999 | Hillman et al. |
| 5,959,086 | A | 9/1999 | Iovanna et al. |
| 6,146,628 | A | 11/2000 | Uckun et al. |
| 6,492,499 | B1 | 12/2002 | Hillman et al. |
| RE39,062 | E | 4/2006 | Vinik et al. |
| RE39,299 | E | 9/2006 | Vinik et al. |
| RE39,351 | E | 10/2006 | Vinik et al. |
| 7,393,919 | B2 | 7/2008 | Levetan et al. |
| 2003/0212000 | A1 | 11/2003 | Van Antwerp |
| 2007/0224638 | A1 | 9/2007 | Melanitou-McClymont |

FOREIGN PATENT DOCUMENTS

| | | |
|---|---|---|
| JP | 07-291114 A | 11/1995 |
| WO | 2007071437 A2 | 6/2007 |

OTHER PUBLICATIONS

Whitcomb, D. C. (2006). "Clinical practice. Acute pancreatitis." N Engl J Med 354(20): 2142-50.
Wright, J. R., R. E. Wager, S. Hawgood, L. Dobbs, and J. A. Clements. 1987. Surfactant apoprotein Mr__ 26,000-36,000 enhances uptake of liposomes by type II cells. J. Biol. Chem. 262: 2888-2894.
Yilmaz, S., M. Widersten, et al. (1995). "Generation of a Ni(II) binding site by introduction of a histidine cluster in the structure of human glutathione transferase A1-1." Protein Eng 8(11): 1163-9.
Yoshioka, S., S. Fujii, et al. (2002). "Gonadotropin-induced expression of pancreatitis-associated protein-III mRNA in the rat ovary at the time of ovulation." J Endocrinol 174(3): 485-92.
Zelensky, A. N., and J. E. Gready. 2003. Comparative analysis of structural properties of the C-type-lectin-like domain (CTLD). Proteins 52: 466-477.
Zelensky, A. N., and J. E. Gready. 2005. The C-type lectin-like domain superfamily. FEBS J. 272: 6179-6217.
Zenilman, M. E., D. Tuchman, et al. (2000). "Comparison of reg I and reg III levels during acute pancreatitis in the rat." Ann Surg 232(5): 646-52.
Zhang, H., E. Kandil, Y. Y. Lin, G. Levi, and M. E. Zenilman. 2004. Targeted inhibition of gene expression of pancreatitis-associated proteins exacerbates the severity of acute pancreatitis in rats. Scand. J. Gastroenterol. 39: 870-881.
Averill, S., D. R. Davis, et al. (2002). "Dynamic pattern of reg-2 expression in rat sensory neurons after peripheral nerve injury." J Neurosci 22(17): 7493-501.
Bodeker, H., V. Keim, et al. (1999). "PAP I interacts with itself, PAP II, PAP III, and lithostathine/reglalpha." Mol Cell Biol Res Commun 2(3): 150-4.
Cambi, A., and C. G. Figdor. 2003. Dual function of C-type lectin-like receptors in the immune system. Curr. Opin. Cell. Biol. 15: 539-546.
Cash, H. L., C. V. Whitham, et al. (2006). "Symbiotic bacteria direct expression of an intestinal bactericidal lectin." Science 313(5790): 1126-30.
Cash, H. L., C. V. Whitham, et al. (2006). "Refolding, purification, and characterization of human and murine RegIII proteins expressed in *Escherichia coli*." Protein Expr Purif 48(1): 151-9.
Chakraborty, C., M. Vrontakis, et al. (1995). "Expression of pituitary peptide 23 in the rat uterus: regulation by estradiol." Mol Cell Endocrinol 108(1-2): 149-54.
Correa, I., and D. H. Raulet. 1995. Binding of diverse peptides to MHC class I molecules inhibits target cell lysis by activated natural killer cells. Immunity 2: 61-71.
De Reggi, M., C. Capon, et al. (1995). "The glycan moiety of human pancreatic lithostathine. Structure characterization and possible pathophysiological implications." Eur J Biochem 230(2): 503-10.
Drickamer, K. 1988. Two distinct classes of carbohydrate-recognition domains in animal lectins. J. Biol. Chem. 263: 9557-9560.
Drickamer, K. 1999. C-type lectin-like domains. Curr. Opin. Struct. Biol. 9: 585-590. Dusetti, N. J., J. M. Frigerio, et al. (1993). "Structural organization of the gene encoding the rat pancreatitis-associated protein. Analysis of its evolutionary history reveals an ancient divergence from the other carbohydrate-recognition domain-containing genes." J Biol Chem 268(19): 14470-5.
Dusetti, N. J., E. M. Ortiz, et al. (1995). "Pancreatitis-associated protein I (PAP I), an acute phase protein induced by cytokines. Identification of two functional interleukin-6 response elements in the rat PAP I promoter region." J Biol Chem 270(38): 22417-21.
Espey, L. L. and J. S. Richards (2002). "Temporal and spatial patterns of ovarian gene transcription following an ovulatory dose of gonadotropin in the rat." Biol Reprod 67(6): 1662-70.
Folch-Puy, E., A. Garcia-Movtero, J. L. Iovanna, J. C. Dagorn, N. Prats, M. I. Vaccaro, and D. Closa. 2003. The pancreatitis-associated protein induces lung inflammation in the rat through activation of TNFalphaexpression in hepatocytes. J. Pathol. 199: 398-408.
Folch-Puy, E., S. Granell, et al. (2006). "Pancreatitis-associated protein I suppresses NF-kappa B activation through a JAK/STAT-mediated mechanism in epithelial cells." J Immunol 176(6): 3774-9.

(Continued)

*Primary Examiner* — Nashaat Nashed
(74) *Attorney, Agent, or Firm* — Hoffmann & Baron, LLP

(57) ABSTRACT

A method of treating pancreatitis is provided, including the steps of: providing a mammal having pancreatitis; and administering a therapeutically effective amount of a truncated N-terminal PAP2; and making of an antibody specifically directed to detect PAP2.

10 Claims, 14 Drawing Sheets

OTHER PUBLICATIONS

Gironella, M., J. L. Iovanna, M. Sans, F. Gil, M. Penalva, D. Closa, R. Miguel, J. M. Pique, and J. Panes. 2005. Anti-inflammatory effects of pancreatitis associated protein in inflammatory bowel disease. Gut 54: 1244-1253.

Graf, R., M. Schiesser, G. A. Scheele, K. Marquardt, T. W. Frick, R. W. Ammann, and D. Bimmler. 2001. A family of 16-kDa pancreatic secretory stress proteins form highly organized fibrillar structures upon tryptic activation. J. Biol. Chem. 276: 21028-21038.

Graf, R., M. Schiesser, et al. (2002). "Coordinate regulation of secretory stress proteins (PSP/reg, PAP I, PAP II, and PAP III) in the rat exocrine pancreas during experimental acute pancreatitis." J Surg Res 105(2): 136-44.

Guthmann, M. D., M. Tal, and I. Pecht. 1995. A new member of the C-type lectin family is a modulator of the mast cell secretory response. Int. Arch. Allergy Immunol. 107: 82-86.

Heller, A., F. Fiedler, et al. (1999). "Pancreatitis-associated protein protects the lung from leukocyte-induced injury." Anesthesiology 91(5): 1408-14.

Ho, M. R., Y. C. Lou, et al. (2006). "Human pancreatitis-associated protein forms fibrillar aggregates with a native-like conformation." J Biol Chem 281(44): 33566-76.

Iobst, S. T., M. R. Wormald, W. I. Weis, R. A. Dwek, and K. Drickamer. 1994. Binding of sugar ligands to Ca2—dependent animal lectins. I. Analysis of mannose binding by site-directed mutagenesis and NMR. J. Biol. Chem. 269: 15505-15511.

Iovanna, J., B. Orelle, et al. (1991). "Messenger RNA sequence and expression of rat pancreatitis-associated protein, a lectin-related protein overexpressed during acute experimental pancreatitis." J Biol Chem 266(36): 24664-9.

Iovanna, J., J. M. Fiderio, et al. (1993). "Lithostathine, an inhibitor of CaCO3 crystal growth in pancreatic juice, induces bacterial aggregation." Pancreas 8(5): 597-601.

Iovanna, J. L. and J. C. Dagorn (2005). "The multifunctional family of secreted proteins containing a C-type lectin-like domain linked to a short N-terminal peptide." Biochim Biophys Acta 1723(1-3): 8-18.

Kandil, E., Y. Y. Lin, et al. (2006). "Dexamethasone mediates protection against acute pancreatitis via upregulation of pancreatitis-associated proteins." World J Gastroenterol 12(42): 6806-11.

Keim, V., and H. G. Loffler. 1986. Pancreatitis-associated protein in bile acidinduced pancreatitis of the rat. Clin. Physiol. Biochem. 4: 136-142.

Kong, S. W., N. Bodyak, et al. (2005). "Genetic expression profiles during physiological and pathological cardiac hypertrophy and heart failure in rats." Physiol Genomics 21(1): 34-42.

Krones, C. J., B. Klosterhalfen, et al. (2005). "Missing effects of zinc in a porcine model of recurrent endotoxemia." BMC Surg 5: 22.

Li, Y. M., G. Baviello, H. Vlassara, and T. Mitsuhashi. 1997. Glycation products in aged thioglycollate medium enhance the elicitation of peritoneal macrophages. J. Immunol. Methods 201: 183-188.

Mayerle J, Hlouschek V, Lerch MM. Current management of acute pancreatitis. Nat Clin Pract Gastroenterol Hepatol. 2005;2:473-83.

McGreal, E. P., L. Martinez-Pomares, and S. Gordon. 2004. Divergent roles for C-type lectins expressed by cells of the innate immune system. Mol. Immunol. 41: 1109-1121.

McKie, A. T., R. J. Simpson, S. Ghosh, T. J. Peters, and F. Farzaneh. 1996. Regulation of pancreatitis-associated protein (HIP/PAP) mRNA levels in mouse pancreas and small intestine. Clin. Sci. 91: 213-218.

Namikawa, K., M. Fukushima, K. Murakami, A. Suzuki, S. Takasawa, H. Okamoto, and H. Kiyama. 2005. Expression of Reg/PAP family members during motor nerve regeneration in rat. Biochem. Biophys. Res. Commun. 332: 126-134.

Namikawa, K., T. Okamoto, et al. (2006). "Pancreatitis-associated protein-III is a novel macrophage chemoattractant implicated in nerve regeneration." J Neurosci 26(28): 7460-7.

Nishimune, H., S. Vasseur, S. Wiese, M. C. Birling, B. Holtmann, M. Sendtner, J. L. Iovanna, and C. E. Henderson. 2000. Reg-2 is a motoneuron neurotrophic factor and a signalling intermediate in the CNTF survival pathway. Nat Cell Biol. 2: 906-914.

Ogawa, H., K. Fukushima, et al. (2003). "Increased expression of HIP/PAP and regenerating gene III in human inflammatory bowel disease and a murine bacterial reconstitution model." Inflamm Bowel Dis 9(3): 162-70.

Ogawa, T., T. Chijiwa, N. Oda-Ueda, and M. Ohno. 2005. Molecular diversity and accelerated evolution of C-type lectin-like proteins from snake venom. Toxicon 45: 1-14.

Orelle, B., V. Keim, et al. (1992). "Human pancreatitis-associated protein. Messenger RNA cloning and expression in pancreatic diseases." J Clin Invest 90(6): 2284-91.

Pandol, S. J., A. K. Saluja, et al. (2007). "Acute pancreatitis: bench to the bedside." Gastroenterology 132(3): 1127-51.

Satomura Y, Sawabu N, Mouri I, Yamakawa O, Watanabe H, Motoo Y, Okai T, Ito T, Kaneda K, Okamoto H. Measurement of serum PSP/reg—protein concentration in various diseases with a newly developed enzyme-linked immunosorbent assay. J Gastroenterol 1995;30:643-50.

Vasseur, S., E. Folch-Puy, V. Hlouschek, S. Garcia, F. Fiedler, M. M. Lerch, J. C. Dagorn, D. Closa, and J. L. Iovanna. 2004. p8 improves pancreatic response to acute pancreatitis by enhancing the expression of the anti-inflammatory protein pancreatitis-associated protein I. J. Biol. Chem. 279: 7199-7207.

Viterbo D, B. M., Lin YY, Murray S, Ocasio V, Mueller C, DiMaio T, Zenilman M. (2004). "Anti-reg antibodies worsen pancreatitis in vivo." Pancreas 29:340.

Viterbo, D., M. H. Bluth, Y.-y. Lin, C. M. Mueller, R. Wadgaonkar, and M. E. Zenilman. 2008. Pancreatitis-associated protein 2 modulates inflammatory responses in macrophages. J. Immunol. 181: 1948-1958.

Weis, W. I., R. Kahn, R. Fourme, K. Drickamer, and W. A. Hendrickson. 1991. Structure of the calcium-dependent lectin domain from a rat mannose-binding protein determined by MAD phasing. Science 254: 1608-1615.

Weis, W. I., K. Drickamer, and W. A. Hendrickson. 1992. Structure of a C-type mannose-binding protein complexed with an oligosaccharide. Nature 360: 127-134.

Wellinghausen, N., A. B. Schromm, et al. (1996). "Zinc enhances lipopolysaccharide-induced monokine secretion by alteration of fluidity state of lipopolysaccharide." J Immunol 157(7): 3139-45.

SEQUENCE LISTING

<160> NUMBER OF SEQ ID NOS: 52

<210> SEQ ID NO 1
<211> LENGTH: 122
<212> TYPE: PRT
<213> ORGANISM: Artificial Sequence
<220> FEATURE:
<223> OTHER INFORMATION: N-truncated PAP2 (28-149)

<400> SEQUENCE: 1

```
Leu Val Thr Thr Leu Lys Ser Trp Phe Gln Ala Asp Leu Ala Cys Gln
1               5                   10                  15

Lys Arg Pro Ser Gly His Leu Val Ser Ile Leu Ser Gly Gly Glu Ala
            20                  25                  30

Ser Phe Val Ser Ser Leu Val Thr Gly Arg Val Asn Asn Asn Gln Asp
        35                  40                  45

Ile Trp Ile Trp Leu His Asp Pro Thr Met Gly Gln Gln Pro Asn Gly
    50                  55                  60

Gly Gly Trp Glu Trp Ser Asn Ser Asp Val Leu Asn Tyr Leu Asn Trp
65                  70                  75                  80

Asp Gly Asp Pro Ser Ser Thr Val Asn Arg Gly Asn Cys Gly Ser Leu
                85                  90                  95

Thr Ala Thr Ser Glu Phe Leu Lys Trp Gly Asp His His Cys Asp Val
            100                 105                 110

Glu Leu Pro Phe Val Cys Lys Phe Lys Gln
        115                 120
```

<210> SEQ ID NO 2
<211> LENGTH: 119
<212> TYPE: PRT
<213> ORGANISM: Artificial Sequence
<220> FEATURE:
<223> OTHER INFORMATION: C-truncation PAP2 (1-119)

<400> SEQUENCE: 2

```
Glu Asp Ser Gln Lys Ala Val Pro Ser Thr Arg Thr Ser Cys Pro Met
1               5                   10                  15

Gly Ser Lys Ala Tyr Arg Ser Tyr Cys Tyr Thr Leu Val Thr Thr Leu
            20                  25                  30

Lys Ser Trp Phe Gln Ala Asp Leu Ala Cys Gln Lys Arg Pro Ser Gly
        35                  40                  45

His Leu Val Ser Ile Leu Ser Gly Gly Glu Ala Ser Phe Val Ser Ser
    50                  55                  60

Leu Val Thr Gly Arg Val Asn Asn Asn Gln Asp Ile Trp Ile Trp Leu
65                  70                  75                  80

His Asp Pro Thr Met Gly Gln Gln Pro Asn Gly Gly Gly Trp Glu Trp
                85                  90                  95

Ser Asn Ser Asp Val Leu Asn Tyr Leu Asn Trp Asp Gly Asp Pro Ser
            100                 105                 110

Ser Thr Val Asn Arg Gly Asn
        115
```

<210> SEQ ID NO 3
<211> LENGTH: 24
<212> TYPE: DNA
<213> ORGANISM: Artificial Sequence
<220> FEATURE:
<223> OTHER INFORMATION: Cysteine 42 Primer Forward

```
<400> SEQUENCE: 3
gtaactctga cgtactgaat tatc                                          24

<210> SEQ ID NO 4
<211> LENGTH: 23
<212> TYPE: DNA
<213> ORGANISM: Artificial Sequence
<220> FEATURE:
<223> OTHER INFORMATION: Cysteine 42 Primer Reverse

<400> SEQUENCE: 4
cttagtggag gtgaggcttc ctt                                           23

<210> SEQ ID NO 5
<211> LENGTH: 23
<212> TYPE: DNA
<213> ORGANISM: Artificial Sequence
<220> FEATURE:
<223> OTHER INFORMATION: Cysteine 120 Primer Forward

<400> SEQUENCE: 5
tatctcaact gggatgggga tcc                                           23

<210> SEQ ID NO 6
<211> LENGTH: 27
<212> TYPE: DNA
<213> ORGANISM: Artificial Sequence
<220> FEATURE:
<223> OTHER INFORMATION: Cysteine 120 Primer Reverse

<400> SEQUENCE: 6
ttcctctact gtcaaccgtg gtaactg                                       27

<210> SEQ ID NO 7
<211> LENGTH: 29
<212> TYPE: DNA
<213> ORGANISM: Artificial Sequence
<220> FEATURE:
<223> OTHER INFORMATION: Cysteine 137 Primer Forward

<400> SEQUENCE: 7
ggagaccatc actctgatgt ggaattacc                                     29

<210> SEQ ID NO 8
<211> LENGTH: 29
<212> TYPE: DNA
<213> ORGANISM: Artificial Sequence
<220> FEATURE:
<223> OTHER INFORMATION: Cysteine 137 Primer Reverse

<400> SEQUENCE: 8
ggtaattcca catcagagtg atggtctcc                                     29

<210> SEQ ID NO 9
<211> LENGTH: 33
<212> TYPE: DNA
<213> ORGANISM: Artificial Sequence
<220> FEATURE:
<223> OTHER INFORMATION: Cysteine 145 Primer Forward

<400> SEQUENCE: 9
ggaattacct tttgtctcca agttcaagca gta                                33

<210> SEQ ID NO 10
<211> LENGTH: 33
<212> TYPE: DNA
```

```
<213> ORGANISM: Artificial Sequence
<220> FEATURE:
<223> OTHER INFORMATION: Cysteine 145 Prime Reverse

<400> SEQUENCE: 10
tactgcttga acttggagac aaaaggtaat tcc                          33

<210> SEQ ID NO 11
<211> LENGTH: 21
<212> TYPE: DNA
<213> ORGANISM: Artificial Sequence
<220> FEATURE:
<223> OTHER INFORMATION: Real-Time PCR IL-1 alpha Forward Primer

<400> SEQUENCE: 11
agcccatgat ttagagacca t                                       21

<210> SEQ ID NO 12
<211> LENGTH: 22
<212> TYPE: DNA
<213> ORGANISM: Artificial Sequence
<220> FEATURE:
<223> OTHER INFORMATION: Real-Time PCR IL-1 alpha Reverse Primer

<400> SEQUENCE: 12
tgatgaactc ctgcttgacg at                                      22

<210> SEQ ID NO 13
<211> LENGTH: 32
<212> TYPE: DNA
<213> ORGANISM: Artificial Sequence
<220> FEATURE:
<223> OTHER INFORMATION: Real-Time PCR IL-1 alpha Probe

<400> SEQUENCE: 13
cagatcagca cctcacagct tccagaataa tt                           32

<210> SEQ ID NO 14
<211> LENGTH: 22
<212> TYPE: DNA
<213> ORGANISM: Artificial Sequence
<220> FEATURE:
<223> OTHER INFORMATION: Real-Time PCR IL-1 beta Forward Primer

<400> SEQUENCE: 14
ccaagcacct tcttttcctt ca                                      22

<210> SEQ ID NO 15
<211> LENGTH: 22
<212> TYPE: DNA
<213> ORGANISM: Artificial Sequence
<220> FEATURE:
<223> OTHER INFORMATION: Real-Time PCR IL-1 beta Reverse Primer

<400> SEQUENCE: 15
agcctgcagt gcagctgtct aa                                      22

<210> SEQ ID NO 16
<211> LENGTH: 28
<212> TYPE: DNA
<213> ORGANISM: Artificial Sequence
<220> FEATURE:
<223> OTHER INFORMATION: Real-Time PCR IL-1 beta Probe

<400> SEQUENCE: 16
agcccgtcct ctgtgactcg tgggatga                                28
```

-continued

```
<210> SEQ ID NO 17
<211> LENGTH: 25
<212> TYPE: DNA
<213> ORGANISM: Artificial Sequence
<220> FEATURE:
<223> OTHER INFORMATION: Real-Time PCR IL-6 Forward Primer

<400> SEQUENCE: 17
tccaaactgg atataaccag gaaat                                           25

<210> SEQ ID NO 18
<211> LENGTH: 32
<212> TYPE: DNA
<213> ORGANISM: Artificial Sequence
<220> FEATURE:
<223> OTHER INFORMATION: Real-Time PCR IL-6 Reverse Primer

<400> SEQUENCE: 18
ttgtctttct tgttatcttg taagttgttc tt                                   32

<210> SEQ ID NO 19
<211> LENGTH: 33
<212> TYPE: DNA
<213> ORGANISM: Artificial Sequence
<220> FEATURE:
<223> OTHER INFORMATION: Real-Time PCR IL-6 Probe

<400> SEQUENCE: 19
aatctgctct ggtcttctgg agttccgttt cta                                  33

<210> SEQ ID NO 20
<211> LENGTH: 25
<212> TYPE: DNA
<213> ORGANISM: Artificial Sequence
<220> FEATURE:
<223> OTHER INFORMATION: Real-Time PCR TNF alpha Forward Primer

<400> SEQUENCE: 20
gaccctcaca ctcagatcat cttct                                           25

<210> SEQ ID NO 21
<211> LENGTH: 23
<212> TYPE: DNA
<213> ORGANISM: Artificial Sequence
<220> FEATURE:
<223> OTHER INFORMATION: Real-Time PCR TNF alpha Reverse Primer

<400> SEQUENCE: 21
ttgtctttga gatccatgcc att                                             23

<210> SEQ ID NO 22
<211> LENGTH: 25
<212> TYPE: DNA
<213> ORGANISM: Artificial Sequence
<220> FEATURE:
<223> OTHER INFORMATION: Real-Time PCR TNF alpha Probe

<400> SEQUENCE: 22
acgtcgtagc aaaccaccaa gcgga                                           25

<210> SEQ ID NO 23
<211> LENGTH: 42
<212> TYPE: DNA
```

```
<213> ORGANISM: Artificial Sequence
<220> FEATURE:
<223> OTHER INFORMATION: Forward Primer-5'

<400> SEQUENCE: 23
agcagaattc gaagactccc agaaggcagt gccctctaca cg                     42

<210> SEQ ID NO 24
<211> LENGTH: 51
<212> TYPE: DNA
<213> ORGANISM: Artificial Sequence
<220> FEATURE:
<223> OTHER INFORMATION: Reverse Primer-5'

<400> SEQUENCE: 24
ctcactcgag gtctactgct tgaacttgca gacaaaaggt aattccacat c           51

<210> SEQ ID NO 25
<211> LENGTH: 31
<212> TYPE: PRT
<213> ORGANISM: Artificial Sequence
<220> FEATURE:
<223> OTHER INFORMATION: Polyclonal Rabbit Anti-rat PAP2

<400> SEQUENCE: 25

Thr Met Gly Gln Gln Pro Asn Gly Gly Gly Trp Glu Trp Ser Asn Ser
1               5                   10                  15

Asp Val Leu Asn Tyr Leu Asn Trp Asp Gly Asp Pro Ser Ser Thr
            20                  25                  30

<210> SEQ ID NO 26
<211> LENGTH: 42
<212> TYPE: DNA
<213> ORGANISM: Artificial Sequence
<220> FEATURE:
<223> OTHER INFORMATION: Primer EcoRI

<400> SEQUENCE: 26
agcagaattc gaagactccc agaaggcagt gccctctaca cg                     42

<210> SEQ ID NO 27
<211> LENGTH: 51
<212> TYPE: DNA
<213> ORGANISM: Artificial Sequence
<220> FEATURE:
<223> OTHER INFORMATION: XhoI

<400> SEQUENCE: 27
ctcactcgag gtctactgct tgaacttgca gacaaaaggt aattccacat c           51

<210> SEQ ID NO 28
<211> LENGTH: 149
<212> TYPE: PRT
<213> ORGANISM: Artificial Sequence
<220> FEATURE:
<223> OTHER INFORMATION: Translated PAP2 Sequence

<400> SEQUENCE: 28

Glu Asp Ser Gln Lys Ala Val Pro Ser Thr Arg Thr Ser Cys Pro Met
1               5                   10                  15

Gly Ser Lys Ala Tyr Arg Ser Tyr Cys Tyr Thr Leu Val Thr Thr Leu
            20                  25                  30

Lys Ser Trp Phe Gln Ala Asp Leu Ala Cys Gln Lys Arg Pro Ser Gly
        35                  40                  45
```

His Leu Val Ser Ile Leu Ser Gly Gly Glu Ala Ser Phe Val Ser Ser
 50                  55                  60

Leu Val Thr Gly Arg Val Asn Asn Asn Gln Asp Ile Trp Ile Trp Leu
65                  70                  75                  80

His Asp Pro Thr Met Gly Gln Gln Pro Asn Gly Gly Trp Glu Trp
                85                  90                  95

Ser Asn Ser Asp Val Leu Asn Tyr Leu Asn Trp Asp Gly Asp Pro Ser
            100                 105                 110

Ser Thr Val Asn Arg Gly Asn Cys Gly Ser Leu Thr Ala Thr Ser Glu
        115                 120                 125

Phe Leu Lys Trp Gly Asp His His Cys Asp Val Glu Leu Pro Phe Val
130                 135                 140

Cys Lys Phe Lys Gln
145

<210> SEQ ID NO 29
<211> LENGTH: 31
<212> TYPE: PRT
<213> ORGANISM: Artificial Sequence
<220> FEATURE:
<223> OTHER INFORMATION: Peptide Sequence Used to Generate anti-PAP2
      Antibody

<400> SEQUENCE: 29

Thr Met Gly Gln Gln Pro Asn Gly Gly Trp Glu Trp Ser Asn Ser
1               5                   10                  15

Asp Val Leu Asn Tyr Leu Asn Trp Asp Gly Asp Pro Ser Ser Thr
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Rat PAP2 Peptide

<400> SEQUENCE: 30

Thr Met Gly Gln Gln Pro Asn Gly Gly Trp Glu Trp Ser Asn Ser
1               5                   10                  15

Asp Val Leu Asn Tyr Leu Asn Trp Asp Gly Asp Pro Ser Ser
            20                  25                  30

<210> SEQ ID NO 31
<211> LENGTH: 31
<212> TYPE: PRT
<213> ORGANISM: Artificial Sequence
<220> FEATURE:
<223> OTHER INFORMATION: Rat Reg1 Sequence

<400> SEQUENCE: 31

Gly Leu His Asp Pro Lys Asn Asn Arg Arg Trp His Trp Ser Ser Gly
1               5                   10                  15

Ser Leu Phe Leu Tyr Lys Ser Trp Asp Thr Gly Tyr Pro Asn Asn
            20                  25                  30

<210> SEQ ID NO 32
<211> LENGTH: 20
<212> TYPE: DNA
<213> ORGANISM: Artificial Sequence
<220> FEATURE:
<223> OTHER INFORMATION: Gene IL-1 alpha Forward Primer

<400> SEQUENCE: 32
gttcctgact tgtttgaaga                                             20

<210> SEQ ID NO 33
<211> LENGTH: 20
<212> TYPE: DNA
<213> ORGANISM: Artificial Sequence
<220> FEATURE:
<223> OTHER INFORMATION: Gene IL-1 alpha Reverse Primer

<400> SEQUENCE: 33
gatatctgga aatctatcat                                             20

<210> SEQ ID NO 34
<211> LENGTH: 20
<212> TYPE: DNA
<213> ORGANISM: Artificial Sequence
<220> FEATURE:
<223> OTHER INFORMATION: Gene IL- beta Forward Primer

<400> SEQUENCE: 34
tgaactcaac tgtgaaatag                                             20

<210> SEQ ID NO 35
<211> LENGTH: 20
<212> TYPE: DNA
<213> ORGANISM: Artificial Sequence
<220> FEATURE:
<223> OTHER INFORMATION: Gene IL-beta Reverse Primer

<400> SEQUENCE: 35
ccattgctgt ttcctaggaa                                             20

<210> SEQ ID NO 36
<211> LENGTH: 20
<212> TYPE: DNA
<213> ORGANISM: Artificial Sequence
<220> FEATURE:
<223> OTHER INFORMATION: Gene IL-6 Forward Primer

<400> SEQUENCE: 36
ccggagagga gacttcacag                                             20

<210> SEQ ID NO 37
<211> LENGTH: 20
<212> TYPE: DNA
<213> ORGANISM: Artificial Sequence
<220> FEATURE:
<223> OTHER INFORMATION: Gene IL-6 Reverse Primer

<400> SEQUENCE: 37
gagcattgga agttggggta                                             20

<210> SEQ ID NO 38
<211> LENGTH: 20
<212> TYPE: DNA
<213> ORGANISM: Artificial Sequence
<220> FEATURE:
<223> OTHER INFORMATION: Gene TNF alpha Forward Primer

<400> SEQUENCE: 38
actgaacttc ggggtgatcg                                             20

<210> SEQ ID NO 39
<211> LENGTH: 19
<212> TYPE: DNA
<213> ORGANISM: Artificial Sequence

```
<220> FEATURE:
<223> OTHER INFORMATION: Gene TNF alpha Reverse Primer

<400> SEQUENCE: 39
gtggtgagga gcacatagt                                                 19

<210> SEQ ID NO 40
<211> LENGTH: 20
<212> TYPE: DNA
<213> ORGANISM: Artificial Sequence
<220> FEATURE:
<223> OTHER INFORMATION: Gene B-actin Forward Primer

<400> SEQUENCE: 40
ggcattgtca ccaactggga                                                20

<210> SEQ ID NO 41
<211> LENGTH: 20
<212> TYPE: DNA
<213> ORGANISM: Artificial Sequence
<220> FEATURE:
<223> OTHER INFORMATION: Gene B-actin Reverse Primer

<400> SEQUENCE: 41
atcgtactcc tgcttgctga                                                20

<210> SEQ ID NO 42
<211> LENGTH: 149
<212> TYPE: PRT
<213> ORGANISM: Artificial Sequence
<220> FEATURE:
<223> OTHER INFORMATION: Mouse Reg3-alpha

<400> SEQUENCE: 42

Glu Asp Phe Gln Lys Glu Val Pro Ser Pro Arg Thr Ser Cys Pro Met
 1               5                  10                  15

Gly Tyr Lys Ala Tyr Arg Ser His Cys Tyr Ala Leu Val Met Thr Pro
            20                  25                  30

Lys Ser Trp Phe Gln Ala Asp Leu Val Cys Gln Lys Arg Pro Ser Gly
        35                  40                  45

His Leu Val Ser Ile Leu Ser Gly Gly Glu Ala Ser Phe Val Ser Ser
    50                  55                  60

Leu Val Asn Gly Arg Val Asp Asn Tyr Gln Asp Ile Trp Ile Gly Leu
65                  70                  75                  80

His Asp Pro Thr Met Gly Gln Gln Pro Asn Gly Gly Trp Glu Trp
                85                  90                  95

Ser Asn Ser Asp Val Leu Asn Tyr Leu Asn Trp Asp Gly Asp Pro Ser
            100                 105                 110

Ser Thr Val Asn Arg Gly His Cys Gly Ser Leu Thr Ala Ser Ser Gly
        115                 120                 125

Phe Leu Lys Trp Gly Asp Tyr Tyr Cys Asp Gly Thr Leu Pro Phe Val
    130                 135                 140

Cys Lys Phe Lys Gln
145

<210> SEQ ID NO 43
<211> LENGTH: 149
<212> TYPE: PRT
<213> ORGANISM: Artificial Sequence
<220> FEATURE:
<223> OTHER INFORMATION: Mouse Reg3-beta

<400> SEQUENCE: 43
```

```
Glu Asp Ser Leu Lys Asn Ile Pro Ser Ala Arg Ile Ser Cys Pro Lys
1               5                   10                  15

Gly Ser Gln Ala Tyr Gly Ser Tyr Cys Tyr Ala Leu Phe Gln Ile Pro
                20                  25                  30

Gln Thr Trp Glu Asp Ala Glu Leu Ala Cys Gln Lys Arg Pro Gly Gly
            35                  40                  45

His Leu Val Ser Val Leu Asn Ser Ala Glu Ala Ser Phe Leu Ser Ser
    50                  55                  60

Met Val Lys Arg Thr Gly Asn Ser Tyr Gln Tyr Thr Trp Ile Gly Leu
65                  70                  75                  80

His Asp Pro Thr Leu Gly Ala Glu Pro Asn Gly Gly Trp Glu Trp
                85                  90                  95

Ser Asn Asn Asp Val Met Asn Tyr Pro Asn Trp Glu Arg Asn Pro Ser
                100                 105                 110

Thr Ala Leu Asp Arg Ala Glu Cys Gly Ser Leu Ser Arg Ala Ser Gly
            115                 120                 125

Phe Leu Lys Trp Arg Asp Met Thr Cys Glu Val Lys Leu Pro Tyr Val
        130                 135                 140

Cys Lys Phe Thr Gly
145
```

<210> SEQ ID NO 44
<211> LENGTH: 148
<212> TYPE: PRT
<213> ORGANISM: Artificial Sequence
<220> FEATURE:
<223> OTHER INFORMATION: Mouse Reg3-gamma

<400> SEQUENCE: 44

```
Glu Val Ala Lys Lys Asp Ala Pro Ser Ser Arg Ser Ser Cys Pro Lys
1               5                   10                  15

Gly Ser Arg Ala Tyr Gly Ser Tyr Cys Tyr Ala Leu Phe Ser Val Ser
                20                  25                  30

Lys Asn Trp Tyr Asp Ala Asp Met Ala Cys Gln Lys Arg Pro Ser Gly
            35                  40                  45

His Leu Val Ser Val Leu Ser Gly Ala Glu Ala Ser Phe Leu Ser Ser
    50                  55                  60

Met Ile Lys Ser Ser Gly Asn Ser Gly Gln Tyr Val Trp Ile Gly Leu
65                  70                  75                  80

His Asp Pro Thr Leu Gly Tyr Glu Pro Asn Arg Gly Gly Trp Glu Trp
                85                  90                  95

Ser Asn Ala Asp Val Met Asn Tyr Ile Asn Trp Glu Thr Asn Pro Ser
                100                 105                 110

Ser Ser Ser Gly Asn His Cys Gly Thr Leu Ser Arg Ala Ser Gly Phe
        115                 120                 125

Leu Lys Trp Arg Glu Asn Tyr Cys Asn Leu Glu Leu Pro Tyr Val Cys
        130                 135                 140

Lys Phe Lys Ala
145
```

<210> SEQ ID NO 45
<211> LENGTH: 149
<212> TYPE: PRT
<213> ORGANISM: Artificial Sequence
<220> FEATURE:
<223> OTHER INFORMATION: Rat PAP1

<400> SEQUENCE: 45

-continued

```
Glu Asp Ser Pro Lys Lys Ile Pro Ser Ala Arg Ile Ser Cys Pro Lys
1               5                   10                  15

Gly Ser Gln Ala Tyr Gly Ser Tyr Cys Tyr Ala Leu Phe Gln Ile Pro
                20                  25                  30

Gln Thr Trp Phe Asp Ala Glu Leu Ala Cys Gln Lys Arg Pro Glu Gly
            35                  40                  45

His Leu Val Ser Val Leu Asn Val Ala Glu Ala Ser Phe Leu Ala Ser
    50                  55                  60

Met Val Lys Asn Thr Gly Asn Ser Tyr Gln Tyr Thr Trp Ile Gly Leu
65                  70                  75                  80

His Asp Pro Thr Leu Gly Gly Glu Pro Asn Gly Gly Trp Glu Trp
                85                  90                  95

Ser Asn Asn Asp Ile Met Asn Tyr Val Asn Trp Glu Arg Asn Pro Ser
                100                 105                 110

Thr Ala Leu Asp Arg Gly Phe Cys Gly Ser Leu Ser Arg Ser Ser Gly
            115                 120                 125

Phe Leu Arg Trp Arg Asp Thr Thr Cys Glu Val Lys Leu Pro Tyr Val
        130                 135                 140

Cys Lys Phe Thr Cys
145
```

<210> SEQ ID NO 46
<211> LENGTH: 149
<212> TYPE: PRT
<213> ORGANISM: Artificial Sequence
<220> FEATURE:
<223> OTHER INFORMATION: Rat PAP2

<400> SEQUENCE: 46

```
Glu Asp Ser Gln Lys Ala Val Pro Ser Thr Arg Thr Ser Cys Pro Met
1               5                   10                  15

Gly Ser Lys Ala Tyr Arg Ser Tyr Cys Tyr Thr Leu Val Thr Thr Leu
                20                  25                  30

Lys Ser Trp Phe Gln Ala Asp Leu Ala Cys Gln Lys Arg Pro Ser Gly
            35                  40                  45

His Leu Val Ser Ile Leu Ser Gly Gly Glu Ala Ser Phe Val Ser Ser
    50                  55                  60

Leu Val Thr Gly Arg Val Asn Asn Asn Gln Asp Ile Trp Ile Trp Leu
65                  70                  75                  80

His Asp Pro Thr Met Gly Gln Gln Pro Asn Gly Gly Trp Glu Trp
                85                  90                  95

Ser Asn Ser Asp Val Leu Asn Tyr Leu Asn Trp Asp Gly Asp Pro Ser
                100                 105                 110

Ser Thr Val Asn Arg Gly Asn Cys Gly Ser Leu Thr Ala Thr Ser Glu
            115                 120                 125

Phe Leu Lys Trp Gly Asp His His Cys Asp Val Glu Leu Pro Phe Val
        130                 135                 140

Cys Lys Phe Lys Gln
145
```

<210> SEQ ID NO 47
<211> LENGTH: 148
<212> TYPE: PRT
<213> ORGANISM: Artificial Sequence
<220> FEATURE:
<223> OTHER INFORMATION: Rat PAP3

<400> SEQUENCE: 47

Glu Asp Ala Lys Glu Asp Val Pro Thr Ser Arg Ile Ser Cys Pro Lys
1               5                   10                  15

Gly Ser Arg Ala Tyr Gly Ser Tyr Cys Tyr Ala Leu Phe Ser Val Ser
                20                  25                  30

Lys Ser Trp Phe Asp Ala Asp Leu Ala Cys Gln Lys Arg Pro Ser Cys
            35                  40                  45

His Leu Val Ser Val Leu Ser Gly Ser Glu Ala Ser Phe Val Ser Ser
        50                  55                  60

Leu Ile Lys Ser Ser Gly Asn Ser Gly Gln Asn Val Trp Ile Gly Leu
65                  70                  75                  80

His Asp Pro Thr Leu Gly Gln Glu Pro Asn Arg Gly Gly Trp Glu Trp
                85                  90                  95

Ser Asn Ala Asp Val Met Asn Tyr Phe Asn Trp Glu Thr Asn Pro Ser
            100                 105                 110

Ser Val Ser Gly Ser His Cys Gly Thr Leu Thr Arg Ala Ser Gly Phe
        115                 120                 125

Leu Arg Trp Arg Glu Asn Asn Cys Ile Ser Glu Leu Pro Tyr Val Cys
130                 135                 140

Lys Phe Lys Ala
145

<210> SEQ ID NO 48
<211> LENGTH: 149
<212> TYPE: PRT
<213> ORGANISM: Artificial Sequence
<220> FEATURE:
<223> OTHER INFORMATION: Human PAP

<400> SEQUENCE: 48

Glu Glu Pro Gln Arg Glu Leu Pro Ser Ala Arg Ile Arg Cys Pro Lys
1               5                   10                  15

Gly Ser Lys Ala Tyr Gly Ser His Cys Tyr Ala Leu Phe Leu Ser Pro
                20                  25                  30

Lys Ser Trp Thr Asp Ala Asp Leu Ala Cys Gln Lys Arg Pro Ser Gly
            35                  40                  45

Asn Leu Val Ser Val Leu Ser Gly Ala Glu Gly Ser Phe Val Ser Ser
        50                  55                  60

Leu Val Lys Ser Thr Gly Asn Ser Tyr Ser Tyr Val Trp Ile Gly Leu
65                  70                  75                  80

His Asp Pro Thr Gln Gly Thr Glu Pro Asn Gly Glu Gly Trp Glu Trp
                85                  90                  95

Ser Ser Ser Asp Val Met Asn Tyr Phe Ala Trp Glu Arg Asn Pro Ser
            100                 105                 110

Thr Ile Ser Ser Pro Gly His Cys Ala Ser Leu Ser Arg Ser Thr Ala
        115                 120                 125

Phe Leu Arg Trp Lys Asp Tyr Asn Cys Asn Val Arg Leu Pro Tyr Val
130                 135                 140

Cys Lys Phe Thr Asp
145

<210> SEQ ID NO 49
<211> LENGTH: 149
<212> TYPE: PRT
<213> ORGANISM: Human Reg3

<400> SEQUENCE: 49

Glu Glu Thr Gly Lys Glu Leu Pro Ser Pro Arg Ile Ser Cys Pro Lys
1               5                   10                  15

Gly Ser Lys Ala Tyr Gly Ser Pro Cys Tyr Ala Leu Phe Leu Ser Pro
            20                  25                  30

Lys Ser Trp Met Asp Ala Asp Leu Ala Cys Gln Lys Arg Pro Ser Gly
        35                  40                  45

Lys Leu Val Ser Val Leu Ser Gly Ala Glu Gly Ser Phe Val Ser Ser
50                  55                  60

Leu Val Arg Ser Ile Ser Asn Ser Tyr Ser Tyr Ile Trp Ile Gly Leu
65                  70                  75                  80

His Asp Pro Thr Gln Gly Ser Glu Pro Asp Gly Asp Gly Trp Glu Trp
                85                  90                  95

Ser Ser Thr Asp Val Met Asn Tyr Phe Ala Trp Glu Lys Asn Pro Ser
            100                 105                 110

Thr Ile Leu Asn Pro Gly His Cys Gly Ser Leu Ser Arg Ser Thr Gly
        115                 120                 125

Phe Leu Lys Trp Lys Asp Tyr Asn Cys Asp Ala Lys Leu Pro Tyr Val
130                 135                 140

Cys Lys Phe Lys Asp
145

<210> SEQ ID NO 50
<211> LENGTH: 146
<212> TYPE: PRT
<213> ORGANISM: Artificial Sequence
<220> FEATURE:
<223> OTHER INFORMATION: Canine PAP

<400> SEQUENCE: 50

Glu Asp Ser Gln Lys Asp Val Pro Ala Pro Arg Ile Thr Cys Pro Lys
1               5                   10                  15

Gly Ser Lys Ala Tyr Ala Ser His Cys Tyr Ala Leu Phe Lys Thr Pro
            20                  25                  30

Lys Ser Trp Met Asp Ala Asp Met Ala Cys Gln Lys Arg Pro Ser Gly
        35                  40                  45

His Leu Val Ser Val Leu Ser Gly Ser Glu Ala Ser Phe Val Ala Ser
50                  55                  60

Leu Val Lys Asn Ser Val Asn Ser Tyr Ser Tyr Val Trp Met Gly Leu
65                  70                  75                  80

His Asp Pro Thr Glu Gly Tyr Glu Pro Asn Ala Asp Gly Trp Glu Trp
                85                  90                  95

Ser Ser Ala Asp Ile Leu Asn Tyr Ser Ala Trp Glu Lys Asn Pro Ser
            100                 105                 110

Thr Ile Ala Asn Pro Gly Tyr Cys Gly Ser Leu Ser Arg Ser Thr Gly
        115                 120                 125

Tyr Leu Lys Trp Lys Asp Tyr Asn Cys Ala Thr Lys Leu Pro Tyr Val
130                 135                 140

Cys Lys
145

<210> SEQ ID NO 51
<211> LENGTH: 149
<212> TYPE: PRT
<213> ORGANISM: Artificial Sequence
<220> FEATURE:
<223> OTHER INFORMATION: Sheep PAP

<400> SEQUENCE: 51

```
Gln Glu Pro Glu Ile Lys Leu Leu Ser Glu Arg Ile Ser Cys Pro Arg
1               5                   10                  15

Gly Ala Ile Gly Tyr Gly Ser Tyr Cys Tyr Ala Leu Tyr Lys Ala Ala
            20                  25                  30

Arg Ser Trp Met Gly Ala Asn Ile Ala Cys Gln Lys Arg Pro Ser Gly
        35                  40                  45

His Leu Ala Ser Val Leu Ser Gly Thr Glu Gly Ala Phe Leu Ala Ser
    50                  55                  60

Leu Val Gly Asp Asp Leu Asn Thr His Ser Asp Val Trp Ile Gly Leu
65                  70                  75                  80

His Asp Pro Thr Glu Gly Ser Glu Pro Asn Ala Gly Gly Trp Glu Trp
                85                  90                  95

Ser Ser Thr Asp Val Leu Asn Tyr Phe Ala Trp Glu Arg Ser Pro Ala
            100                 105                 110

Thr Val Ser Asn Pro Gly His Cys Gly Ile Leu Ser Arg Thr Ser Gly
        115                 120                 125

Tyr Leu Lys Trp Lys Asp Tyr Ser Cys His Val Ser Leu Pro Tyr Ile
    130                 135                 140

Cys Lys Phe Lys Gly
145
```

<210> SEQ ID NO 52
<211> LENGTH: 146
<212> TYPE: PRT
<213> ORGANISM: Artificial Sequence
<220> FEATURE:
<223> OTHER INFORMATION: Bovine PAP

<400> SEQUENCE: 52

```
Glu Asp Ser Gln Arg Ser Glu Arg Ile Ser Cys Pro Arg Gly Ser Ile
1               5                   10                  15

Ala Tyr Gly Ser Ser Cys Tyr Val Leu Tyr Lys Val Ala Arg Ser Trp
            20                  25                  30

Met Ser Ala Asn Ile Ala Cys Gln Arg Arg His Ser Gly His Leu Ala
        35                  40                  45

Ser Val Leu Ser Gly Thr Glu Gly Ser Phe Leu Ala Ser Leu Val Arg
    50                  55                  60

Asn Asn Leu Asn Thr Gln Ser Asp Val Trp Ile Gly Leu His Asp Pro
65                  70                  75                  80

Thr Glu Gly Ser Glu Pro Asp Ala Gly Gly Trp Glu Trp Ser Ser Thr
                85                  90                  95

Ala Met Phe Asn Tyr Phe Ala Trp Glu Arg Ile Pro Ser Thr Val Ser
            100                 105                 110

Gly Leu Asp His Cys Gly Ile Leu Ser Arg Thr Ser Gly Tyr Leu Lys
        115                 120                 125

Trp Lys Asn Tyr Asn Cys Asn Val Asn Leu Pro Tyr Ile Cys Gln Phe
    130                 135                 140

Lys Gly
145
```

TRUNCATED PAP2 AND METHODS OF MAKING AND USING SAME

CROSS REFERENCE TO RELATED APPLICATIONS

This application claims priority to U.S. provisional application 61/138,984 filed on Dec. 19, 2008. The provisional application is incorporated herein by reference in its entirety.

FUNDING STATEMENT

This invention was made with government support under contract identifier RO1 DK54511-01 awarded by the National Institute of Health. The government has certain rights in the invention.

FIELD OF THE INVENTION

The invention relates to the use of pancreatic associated proteins (PAP) as a treatment for pancreatic diseases. More specifically, the invention relates to the use of synthetic, truncated PAP in pure form, and its uses in various methods.

BACKGROUND

Acute pancreatitis has a spectrum of severity ranging from a mild, self-limiting course treated with conservative methods, to a more aggressive variety characterized by sepsis, pancreatic necrosis and hemorrhage. It is estimated that 25% of patients with acute pancreatitis will progress in severity and require operative management or die. Pancreatic regenerating protein (Reg) may play a role in the pathophysiology of acute pancreatitis. The regeneration (Reg) family of proteins, which include Reg I (pancreatic stone protein) and Reg III (pancreatitis-associated protein—"PAP"), are a family of proteins minimally expressed in normal pancreas but strongly induced in acute pancreatitis. It has been previously demonstrated that antisense mediated gene knockdown of Reg/PAP in vivo worsens pancreatitis. In those studies, inhibition of Reg/PAP expression significantly worsened pancreatitis in that serum amylase activity, pancreas wet weight, reflecting edema, and serum C-reactive protein levels all increased in antisense-treated animals compared with controls. Furthermore, histopathologic evaluation of pancreas revealed worsened edema, elevated leukocyte infiltration, and fat necrosis after antisense-treatment compared with controls.

The present invention seeks to provide materials and methods which may be suitable for treating and diagnosing pancreatitis through the use of a truncated PAP.

SUMMARY OF THE INVENTION

An aspect of the invention provides a truncated pancreatitis associated protein having an N-terminal truncation amino acids 28-149 of a PAP2, of the sequence listing (SEQ ID. NO 1)
LVTTLKSWFQADLACQKRPSGHLVSILSGGEASFVSSLVTGRVNNNQDIW

IWLHDPTMGQQPNGGGWEWSNSDVLNYLNWDGDPSSTVNRGNCGSLTATS

EFLKWGDHHCDVELPFVCKFKQ.

Another aspect of the invention provides the use of a recombinant truncated pancreatitis associated protein for treatment of pancreatitis.

Yet another aspect of the present invention provides a method of treating pancreatitis, including: providing a mammal having pancreatitis; and administering a therapeutically effective amount of truncated pancreatitis associated protein.

Still another aspect of the present invention provides a method of providing an immunomodulatory effect in a mammal with pancreatitis, including: administering to the mammal in need thereof a therapeutically effective amount of a truncated pancreatitis associated protein.

Still yet another aspect of the present invention provides a method of making recombinant truncated pancreatitis-associated protein including the steps of: inserting a plurality of PAP2 amplicons in-frame into a pET24a bacterial expression vector; growing a plurality of positive clones transformed into a plurality of bacterium to a density in a medium; centrifuging and resuspending the bacterium in a resuspension buffer; sonicating the bacterium with a protease inhibitor; washing a bacterial pellet in a first buffer; washing said bacterial pellet in a second buffer having an amount of urea therein; and resolubilizing the bacterial pellet in resuspension buffer containing an amount of urea.

Another still aspect of the present invention provides a method of screening candidate pancreatitis treatments, including: providing a mammal with a pancreatitis condition; administering to the mammal an amount of a candidate pancreatitis-associated protein having a truncated form; and observing a result thereof.

Another still aspect of the present invention provides a method of making an antibody to portions of pancreatitis associated protein to serve as a diagnostic tool for use in pancreatitis The embodiments of the present invention may be better understood through a study of the following drawings and description.

DETAILED DESCRIPTION OF THE DRAWINGS

Figure 1A:
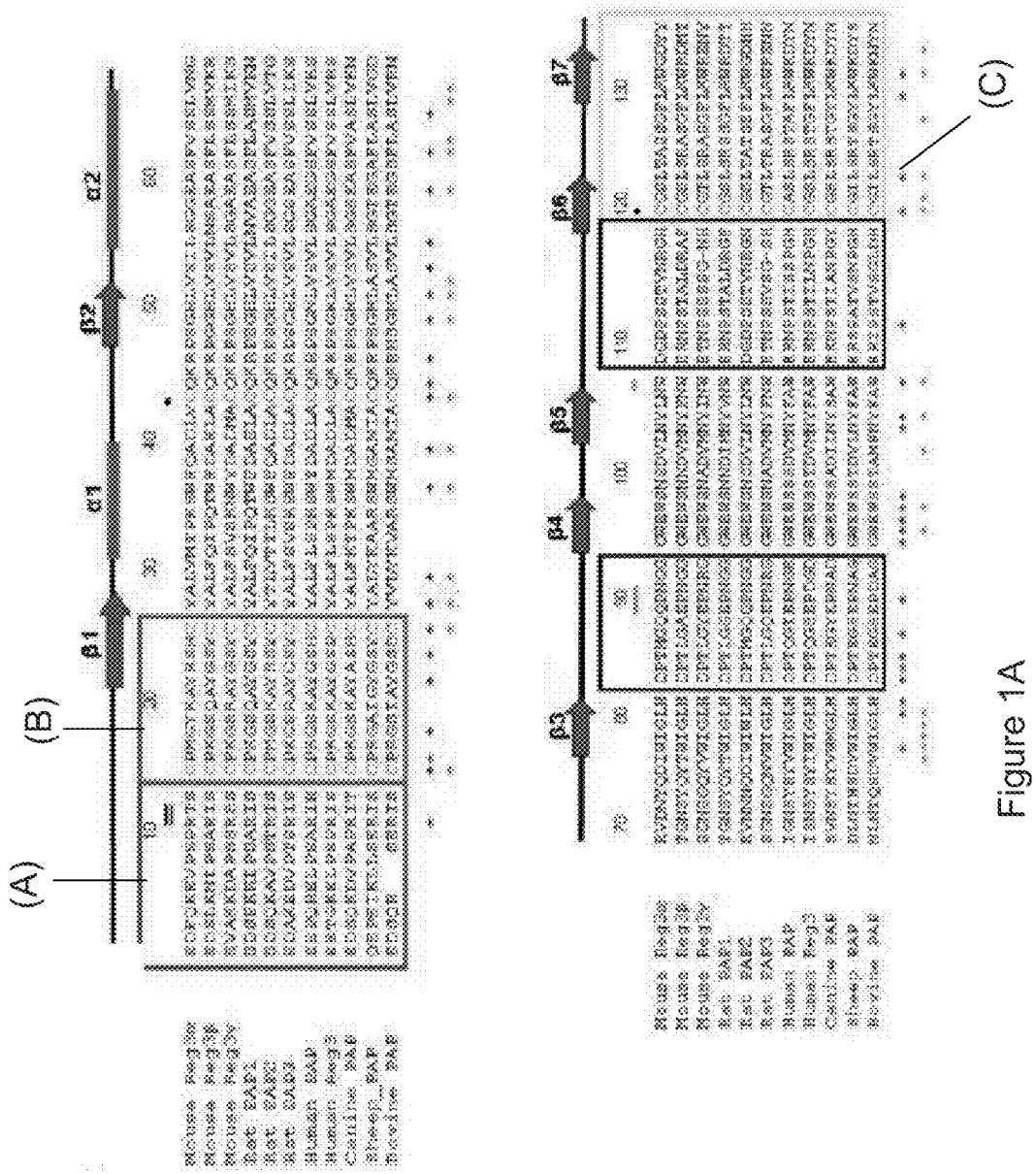
FIG. 1A (parts 1 and 2) depicts the overview of PAP2 structure, specifically a comparative alignment of the amino acid sequence of mouse, rat, human, canine, sheep, bovine PAP isoforms using the clustalW program. The secondary structure is depicted above the primary sequence. The first boxed region (A) corresponds to the N-terminal PAP domain. The C-type lectin long-form domain is the second boxed section (B). The black boxes (unlabeled) correspond to the long loop region. The third boxed region (C), and the region shown in Part 2 correspond to the the C-type lectin consensus sequence. The double line (=) above residues 11-12 specifies the trypsin cleavage site. Cysteines involved in the formation of the three disulfide bonds are highlighted; dots (•) above the indicated cysteines correspond to invariant residues. Lines above the sequences correspond to calcium-binding sites. The top line of asterisks (*) are residues conserved in all PAP proteins. The bottom line of asterisks (*) are conserved residues found in C-type lectin proteins. The sequences are Mouse Reg3α(SEQ. ID. 42), Mouse Reg3β(SEQ. ID. 43), Mouse Reg3γ(SEQ. ID. 44), Rat PAP1 (SEQ. ID. 45), Rat PAP2 (SEQ. ID. 46), Rat PAP3 (SEQ. ID. 47), human PAP (SEQ. ID. 48), Human Reg3 (SEQ. ID. 49), Canine PAP (SEQ. ID. 50), Sheep PAP (SEQ. ID. 51), and Bovine PAP (SEQ. ID. 52).
Figure 1A:
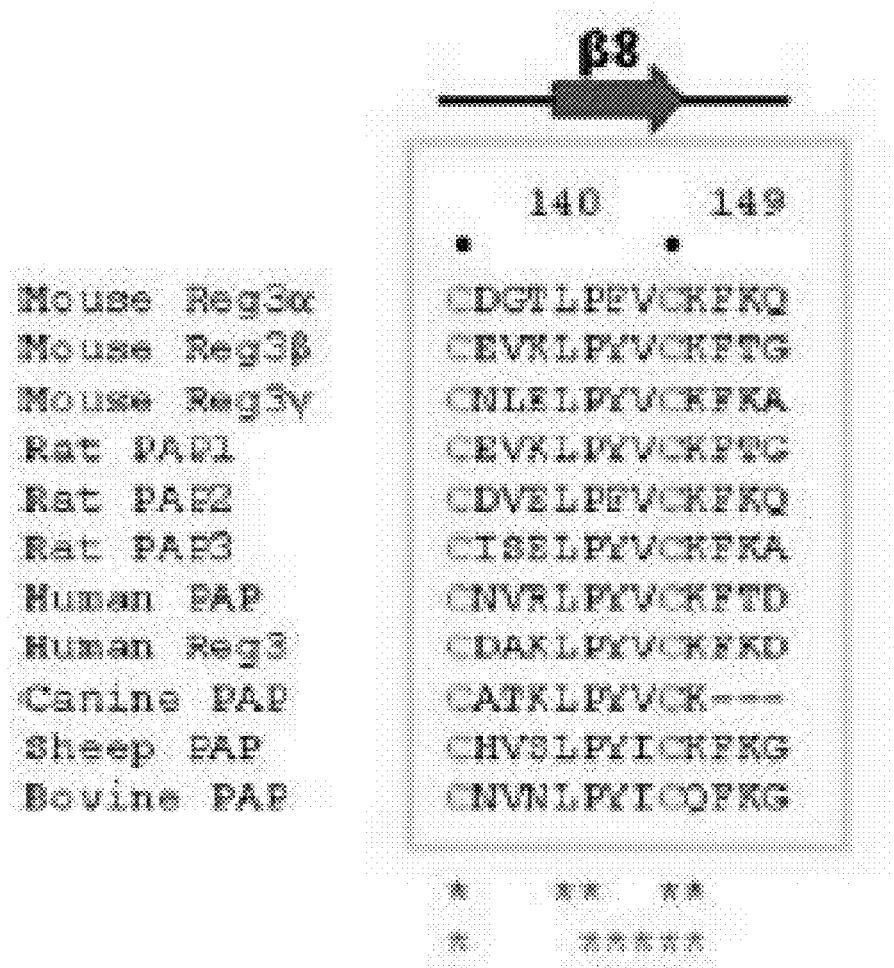

Acute pancreatitis is an acute inflammatory condition of the pancreas that varies widely in presentation, course and outcome. The majority of patients with acute pancreatitis have a mild and manageable disease process. However, approximately 20-30% of patients suffer from a severe episode, which can include organ dysfunction secondary to a systemic inflammatory process. Although a great deal is known regarding etiologic causes of pancreatitis, the molecular and pathophysiologic mechanisms of its disease progression are not fully understood. It has been postulated that the systemic manifestations associated with pancreatitis are mediated by substances released from the pancreas during stress. Pancreatitis is routinely diagnosed by clinical assessment of acute abdomen along with elevated white count, elevated amylase and lipase levels and radiographic findings. Background of Pancreatitis Associated Proteins Pancreatitis associated proteins (PAP), members of the Reg gene family, are 14-17 kDa secretory proteins which have been shown to be strongly induced during acute pancreatitis. They were originally identified during acute pancreatitis, and have been reported in other inflamed pathologic organ systems including Crohn's disease, inflammatory bowel disease, liver injury, neuronal damage, and cardiac tissue damage. Additionally, these proteins have been reported during physiologic inflammatory processes pertaining to the uterus and ovaries. The upregulation of PAP in these diverse conditions is thought to represent a physiologic response induced by tissue damage and is postulated to provide immunomodulatory effects. In rats, there are three highly homologous PAP isoforms, referred to as PAP1, PAP2, and PAP3. The biologic role for each of these proteins has not been fully elucidated but reported studies indicate that they represent a multifunctional group of proteins. Reported functional roles for PAP proteins include apoptosis, cell regeneration and proliferation, carcinogenesis, Alzheimer's disease pathogenesis, immunity, and inflammation.

The present invention relates to the discovery that PAP proteins play regulatory roles during the inflammatory process. The applicants have previously reported that antibody neutralization of PAP in rats with acute pancreatitis caused an increased inflammatory response in the pancreas. Other studies have demonstrated that antisense and siRNA inhibition of PAP correlated with worsening of pancreatitis severity. Regarding the immunomodulatory function of PAP isoforms, other studies showed that PAP1 mediates a decrease in TNFα and IL-6 activation of macrophages. Another supporting study found that in the AR42J acinar cell line, PAP1 inhibits the NFκB pathway via the STAT3/SOC3 pathway. Furthermore, studies have also found that PAP is anti-inflammatory in patients with inflammatory bowel disease. PAP1 was also reported to protect against lung injury.

Conversely, high doses of PAP1 have been shown to induce lung inflammation in rats. The PAP3 isoform has been shown to be a strong macrophage chemokine that is secreted in response to nerve injury. Interestingly, the mouse homolog to PAP3, referred to as Reg3 gamma has been shown to be involved in innate immunity, possessing anti-microbial properties towards gram positive bacteria, specifically binding to the peptidoglycan region of its membrane.

However, unlike PAP1 and PAP3, the physiologic inflammatory relevance of the PAP2 isoform has heretofore not been elucidated. The truncated protein of the invention disclosed herein refers to the rat PAP2 isoform. The C-terminus/disulfide bonds of the protein are important to maintain activity as judged by macrophage TNF production compared with the wild type (and other N terminal truncation mutants).

Pancreatitis-associated protein 2 ("PAP2") is a member of the Reg3 gene family and is classified as a group 7 C-type lectin-like protein. In rats, each of the three PAP isoforms has independent immunologic functional effects on macrophages. The Applicants have previously shown that PAP2 up-regulates inflammatory cytokines in macrophages in a dose-dependent manner and acts through NF-κB mechanisms. With the experiments that led to the present invention, the present invention seeks to determine protein domains that are essential for the immunologic function of PAP2 by mutational or chemical analysis. The protein activity for each mutant was determined by measuring TNF-α, IL-6, or IL-1 production in macrophages.

PAPs are a group of secreted C-type lectin-like proteins that are typically expressed in tissues that are injured and inflamed. Three PAP isoforms are detected in rats and mice whereas two are identified in humans and one is observed in other mammalian species, bovine, canine, and sheep. This is of great importance because rat PAP isoforms are shown to have different immunologic functions. It is not known whether the function for human PAP isoforms encompasses a single element or is multifunctional. Nevertheless, a characteristic feature of PAP proteins is the unique yet simple protein sequence. These proteins are comprised solely of a short N-terminal PAP domain and a large C-type lectin CRD domain that spans the rest of the protein. C-type lectin proteins were initially defined as proteins that are able to bind carbohydrate residues in a calcium-dependent manner. However, this definition is no longer accepted due to the emergence of C-type lectin proteins that are incapable of binding sugar components. Interestingly, studies are beginning to show new functional roles for these atypical C-type lectin proteins, also referred to as C-type lectin-like containing proteins (CTLD). Agreeably, a commonality all proteins in the C-type lectin superfamily share is the formation of the well-known C-type lectin tertiary fold. The C-type lectin fold is a globular structure with two highly conserved α helices, two antiparallel β sheets, six cysteines, and a variable long loop region. It was previously reported the C-type lectin-like protein PAP2 to be a modulator of macrophage function.

The domain architecture for PAP proteins is unlike any other C-type lectin protein which is why they were accordingly situated into their own group, referring to group 7 of the C-type classification system. Interestingly, PAP proteins are the smallest protein reported among the C-type lectin family. Additionally, PAP proteins contain an extended CRD domain that is only associated with long-form C-type lectins. The long-form domain comprises residues 14-25 and encodes for a short β-hairpin that is stabilized by a disulfide formed by $Cys^{14}$ and $Cys^{25}$. Moreover, PAP proteins contain highly conserved residues that are essential for establishing the C-type lectin fold and a partial calcium-binding motif, though a complete absence is noted in rat PAP2 and mouse Reg3α (FIG. 1A). Furthermore, PAP proteins lack residues involved in carbohydrate recognition but contain four invariant cysteines that are important in the formation of three disulfide bonds. In PAP proteins, the domain corresponding to the loop region consists of several discontinuous loop structures that are separated by β sheets.

Pancreatitis-associated proteins (PAP) encompass a family of small evolutionarily conserved C-type lectin proteins that belong to the Reg3 gene family. Derivation of the name PAP followed identification of PAP1 as a robustly expressed protein that was secreted into pancreatic juice by acinar cells during acute pancreatic inflammation. Over its course, ensuing reports detected the expression of PAP proteins in a number of pathologic tissue injuries, as well as physiologic processes. Specific PAP isoforms have been shown to be normal constituents of intestinal paneth cells and, more importantly, serve to maintain gut microbial integrity. PAP proteins also serve important roles within the nervous system, being involved in motor neuron regeneration. Coupling its diffuse expression pattern with the interspecies conservation of this group of proteins supports important functional roles for this network of proteins. The C-type lectin superfamily is a large group of proteins which is characterized as having at least one carbohydrate recognition domain (CRD). Over its course, studies have identified the CRD domain to contain highly conserved residues, motifs, and a consensus sequence. More importantly, the implications of the CRD domain are broad and vary widely in function. This is exhibited by the classification of C-type lectins into 17 subfamilies, which is based on the protein's overall domain architecture.

Conceivably, the variability within the CRD domains produces a range of biologic functions, including ligand-binding sites for oligosaccharides and polypeptide ligands. Moreover, the structural basis pertaining to carbohydrate specificity has been well documented in many C-type lectin proteins. However, structural analysis of C-type lectin that are known to bind protein ligands has not been evaluated. Many C-type lectins actually lack calcium- and carbohydrate binding elements and thereby have been termed C-type lectin-like proteins.

An increasing number of studies are beginning to show that "atypical" C-type lectin-like proteins are involved in regulatory processes pertaining to various aspects of the immune system. Examples of this include the NK cell inhibitory receptor Ly49A C-type lectin-like protein which is shown to complex with the MHC class I ligand, and the C-type lectin-like protein mast cell function-associated Ag which is involved in the inhibition of IgE-FcεRI mediated degranulation of mast cell granules. PAP proteins belong to the group 7 subfamily of C-type lectins, which are speculated to be involved in the regulation of the inflammatory process. Recent studies suggest that PAP proteins are regulatory proteins that are involved in both the anti- and proinflammatory aspects of this process. The Applicants have previously demonstrated that PAP2 mediates the expression of inflammatory cytokines in macrophages through the NF-κB pathway. The Applicants also showed that both antisense gene knockdown and Ab neutralization of PAP2 in rats with experimental acute pancreatitis caused a significant increase in disease severity. These findings corroborate other studies which showed protective roles served by PAP proteins during tissue injury. Taken together, these studies suggest that PAP proteins are key regulators of inflammation and their absence causes a dysregulated inflammatory process.

Truncated PAP2

The Applicants have discovered that synthesis and use of truncated N-terminal PAP2 has various benefits and advantages associated with its use. For example, by using smaller truncated recombinant PAP2, it may be more efficient and effective to synthesize and purify the protein. Also, as the PAP2 is in truncated form, the smaller sized molecule may have increased diffusibility through the cell wall upon administration, which may increase the activity of treatment. Another desirable characteristic is that as the PAP2 is in truncated form, the protein chain may be used for linkers, molecules with other effects, or materials to promote and effectuate transportation to the desired site in situ. Present inventors have surprisingly discovered the truncated form of the N-terminal PAP2 is in its critical context, reduced in size but still with all of the vital components to maintain functionality in use. This truncated N-terminal PAP2 may be used as an effective treatment against pancreatitis. Other uses of the truncated N-terminal PAP2 of the present invention include using PAP2 with serum binding mediators (important in orchestrating progression), as a possible therapeutic cocktail.

Truncation of the first 25 residues on the N terminus of PAP2 were not found to affect protein activity, whereas truncation of the last 30 residues of the C terminus of PAP2 completely inactivated the function of PAP2. Additionally, reduction of three disulfide bonds proved to be important for the activity of this protein. Further investigation revealed two invariant disulfide bonds were important for activity of PAP2 while the disulfide bond that is observed in long-form C-type lectin proteins was not essential for activity. Coupling the ability of PAP2 to up-regulate inflammatory cytokines via NF-κB with its associated expression in acute pancreatitis, a condition with aberrant concentrations of inflammatory cytokines, it was investigated whether PAP2 mutants mechanistically activate the NF-κB-signaling pathway and demonstrate that pre-incubation with select rPAP2 mutant proteins affect translocation of this transcription factor into the nucleus.

The present invention provides a truncated pancreatitis associated protein having an N-terminal truncation (amino acids 28-149) of PAP2, of the sequence listing (SEQ ID NO: 1)
LVTTLKSWFQADLACQKRPSGHLVSILSGGEASFVSSLVTGRVNNNQDIWI

WLHDPTMGQQPNGGGWEWSNSDVLNYLNWDGDPSSTVNRGNCGSLTATSEF

LKWGDHHCDVELPFVCKFKQ.

The N-terminal end truncated PAP2 isoform of PAP may be synthesized in a substantially homologous form. The truncated PAP2 protein is about 90-99% homologous, more desirably at least 95% homologous, and most desirably, about 100% homologous. Furthermore, the N-terminal truncated PAP2 isoform may be purified such that it is in a substantially purified form.

The N-terminal truncated PAP2 may be used in the treatment of pancreatitis. The N-truncated PAP2 may be administered to an animal, preferably a mammal in need thereof in such a dosage and with such an administration to provide a therapeutic result and/or effective treatment of pancreatitis and related conditions to pancreatitis.

Also, the present invention includes a method of treating pancreatitis. In one embodiment, the method of treating pancreatitis may include the steps of providing a mammal having pancreatitis; and administering a therapeutically effective amount of truncated pancreatitis associated protein. The method may further include the step of correlating a result thereof. Correlating a result may be observing treatment and/or analyzing a result to test the effectiveness of a treatment.

The method may also include measuring at least one treatment based result. This may include measuring one or more variables indicative of pancreatitis. Such variables may further include, for example, a clinical assessment of acute abdomen, an elevated white cell count, an elevated amylase, an elevated lipase levels, radiographic findings, and combinations of these variables.

The method may further include the step of observing the NF-κB pathway for a therapeutic result thereof. Through its role as a transcription factor, the NF-κB signaling pathway is a modulator of inflammation in various organ systems. NF-κB mediates the transcription of many proteins, including inflammatory cytokines, adhesion molecules, immunoreceptors, acute phase proteins, enzymes, and anti-apoptotic proteins. As such an important pathway, one or more of the methods of the present invention may include observing the NF-κB pathway. Such observation may be done through traditional experimental and analysis protocols, including performing and observing the results of a various ELISA test, a western blot test, and/or a PCR test.

The present invention further includes a method of providing an immunomodulatory effect in a mammal with pancreatitis. The method may include the step of administering to the mammal in need thereof a therapeutically effective amount of a truncated pancreatitis associated protein. The truncated pancreatitis associated protein is preferably an N-terminal end truncated PAP2 protein. The truncated portion may have one or more amino acids removed therefrom. In one embodiment, the truncated portion may have amino acids 1-25 removed.

Continued study of PAP2 has heretofore been hampered by the ability to effectively isolate appropriate amounts of protein from pancreatic juice or efficient generation of recombinant proteins. Prior to the present invention, PAP2 synthesis and production has been hampered with the difficulty of adequately and effectively isolating or generating purified PAP2 isoforms. This is largely due to the fact that PAP2 isoforms are largely insoluble, thereby precluding efficient extraction from any aqueous phase.

A novel method for the synthesizing truncated PAP2 is provided with the present invention. One such method for synthesizing truncated PAP2 includes using either GST or HIS tagged. Both forms of recombinant proteins function similarly with regard to proinflammatory cytokine expression and bacterial agglutination. Also, the methods of making PAP provide adequate, reproducible results in sufficient quantities of PAP to further study structure and function. Not only is the yield in a sufficient quantity, but also, the final truncated N-terminal rPAP2 or rPAP2 is fully functional.

The present invention further includes a method of making recombinant truncated pancreatitis-associated protein. This method of making recombinant truncated pancreatitis associated protein includes the steps of: inserting a plurality of PAP2 amplicons in-frame into a pET24a bacterial expression vector; growing a plurality of positive clones transformed into a plurality of bacterium (E. Coli) to a density in a medium; centrifuging and resuspending the bacterium in a resuspension buffer; sonicating the bacterium with a protease inhibitor; washing a bacterial pellet in a first buffer, washing said bacterial pelled in a second buffer having an amount of urea therein; and resolubilizing the bacterial pellet in resuspension buffer containing an amount of urea.

The resulting N-truncated rPAP2 may be tagged with a GST tag or a HIS tag (which is roughly six times smaller than the GST tag) for use in experimental analysis and measurements related to the administration and investigation of the function and role of rPAP2. During the method of synthesis, complete rPAP2 may be synthesized and then cleaved to a desired site. Alternatively, a shortened or truncated N-terminal rPAP2 may be synthesized with the method of the present invention.

The method may further include the step of centrifuging the solubilized proteins, followed, optionally, by exclusion and/or affinity chromatography to purify the PAP2. The method may also include a batch purifying step of one or more chromatography fractions containing high levels of PAP2 by combining the fractions onto cation exchange beads. The beads may be eluted and washed with a buffer containing urea. Beads can be were washed and dialyzed in an elution buffer and a dialysis buffer, each containing, inter alia, urea. The eluted protein was then dialyzed in refolding buffer, followed by a dialysis buffer. The dialysis buffer may be repeated as may be desired.

In one embodiment there may be provided a method of screening candidate pancreatitis treatments to determine effectiveness of the desired treatment. In such methods, there is first provided a subject having a pancreatitis condition. Preferably, the subject is a mammal. At least one candidate pancreatitis-associated protein is then administered to the subject. In a preferred embodiment, the pancreatitis-associated protein has a truncated form, desirably an N-terminal truncation of one or more amino acids. After administration, the subject is then observed for any results. The results are then used to analyze the effectiveness of the desired treatment. The method may also include the step of correlating a result thereof. Further, the method may optionally include the step of determining whether the candidate treatment has a pancreatitis inhibiting effect. This determination may be made by observing various physiological characteristics, including inflammation, pain, etc, as is known in the art for diagnosing and observing the condition of pancreatitis in a subject.

Any amount of candidate pancreatitis-associated protein may be administered to the subject, and in one embodiment, a therapeutically effective amount is administered. If desired, the protein may be administered in any amount within a particular range of amounts, based upon the body weight of the subject. For example, the protein may be administered from about 0.1 to about 10 mg per kg of body weight of the subject. More particularly, the protein may be administered in an amount of about 1 to about 3 mg per kg of body weight of the subject. The protein may be administered in any desired form, and in particular is administered through an IV.

When administering the N-truncated rPAP2 to a plurality of cells or to an animal, it may be desirable to administer the N-truncated rPAP2 with a biocompatible material. Such material may increase the effectiveness of the administration by increasing solubility or dispersion of the material in situ. Also, when the N-truncated rPAP2 is administered to a subject, preferably a mammal, more preferably a human, the N-truncated rPAP2 may preferably be administered in a pharmaceutically acceptable carrier.

The N-truncated rPAP2 of the present invention may be administered preferably to a mammal or to a human patient as a pharmaceutical composition containing a therapeutically effective dose the N-truncated rPAP2 according to the present invention together with a pharmaceutical acceptable carrier. The term "therapeutically effective amount" or "pharmaceutically effective amount" means the dose needed to produce in an individual, measurable beneficial effect of the treatment. Preferably, compositions containing the N-truncated rPAP2 of the present invention are administered intravenously for the purpose of treating pancreatitis.

Administration of the N-truncated rPAP2 of the present invention may be oral, intravenous, intranasal, intraperitoneal, intramuscular, intradermal or subcutaneous, by suppository or by infusion or implantation. When administered in such manner, the N-truncated rPAP2 of the present invention may be combined with other ingredients, such as carriers and/or adjuvants. There are no limitations on the nature of the other ingredients, except that they are desirably pharmaceutically acceptable, efficacious for their intended administration, preferably do not degrade the activity of the active ingredients of the compositions, and desirably do not impede transport and importation of the N-truncated rPAP2 into a cell. The N-truncated rPAP2 compositions may also be impregnated into transdermal patches, or contained in subcutaneous inserts, preferably in a liquid or semi-liquid form which patch or insert time-releases therapeutically effective amounts of one or more of the s N-truncated rPAP2.

The pharmaceutical forms suitable for injection include sterile aqueous solutions or dispersions and sterile powders for the extemporaneous preparation of sterile injectable solutions or dispersions. The ultimate solution form in all cases is preferably a sterile material in a fluid form. Typical carriers include a solvent or dispersion medium containing, e.g., water buffered aqueous solutions, i.e., biocompatible buffers, ethanol, polyols such as glycerol, propylene glycol, polyethylene glycol, suitable mixtures thereof, surfactants or vegetable oils. Sterilization may be accomplished utilizing any art-recognized technique, including but not limited to filtration or addition of antibacterial or antifungal agents. Examples of such agents include paraben, chlorbutanol, phenol, sorbic acid or thimerosal. Isotonic agents such as sugars or sodium chloride may also be incorporated into the subject compositions.

As used herein, a "pharmaceutically acceptable carrier" includes any and all solvents, dispersion media, coatings, antibacterial and antifungal agents, isotonic agents and the like. The use of such media and agents are well known in the art.

Production of sterile injectable solutions containing the subject N-truncated rPAP2 is accomplished by incorporating the N-truncated rPAP2 described hereinabove in the required amount in the appropriate solvent with one or more of the various ingredients enumerated above, as required, followed by sterilization, preferably filter sterilization. In order to obtain a sterile powder, the above solutions are vacuum-dried or freeze-dried as necessary.

Inert diluents and/or edible carriers and the like may be part of the pharmaceutical compositions when the N-truncated rPAP2 is administered orally. The pharmaceutical compositions may be in hard or soft shell gelatin capsules, be compressed into tablets, or may be in an elixir, suspension, syrup or the like.

The N-truncated rPAP2 is thus compounded for convenient and effective administration in pharmaceutically effective amounts with a suitable pharmaceutically acceptable carrier in a therapeutically effective dosage. Examples of a pharmaceutically effective amount include N-truncated rPAP2 concentrations in the range from about at least about 0.1 ug/ml to at least about 10 g/ml.

A therapeutically effective amount of the N-truncated rPAP2 to be used in the methods of the invention applied to humans is dependent upon several factors, including the stage of pancreatitis. In addition, the physiological characteristics of the subject may also be factors, including the individual's lean body weight, gender, and overall health. It can be generally stated, however, that the N-truncated rPAP2 of the present invention be administered in any amount, as may be desired. It is also possible to reiterate or readminister the N-truncated rPAP2 pharmaceutical compositions is indicated and preferred. This may be in the form of a course of treatment, therapy, or combination therapy with other agents and/or medicaments. The N-truncated rPAP2 of the present invention may be administered in a manner compatible with the dosage formulation and in such an amount as will be therapeutically effective. Systemic dosages depend on the age, lean body weight, and condition of the patient and the administration route.

Comparison of PAP Conservation Across Species

Figure 1B:
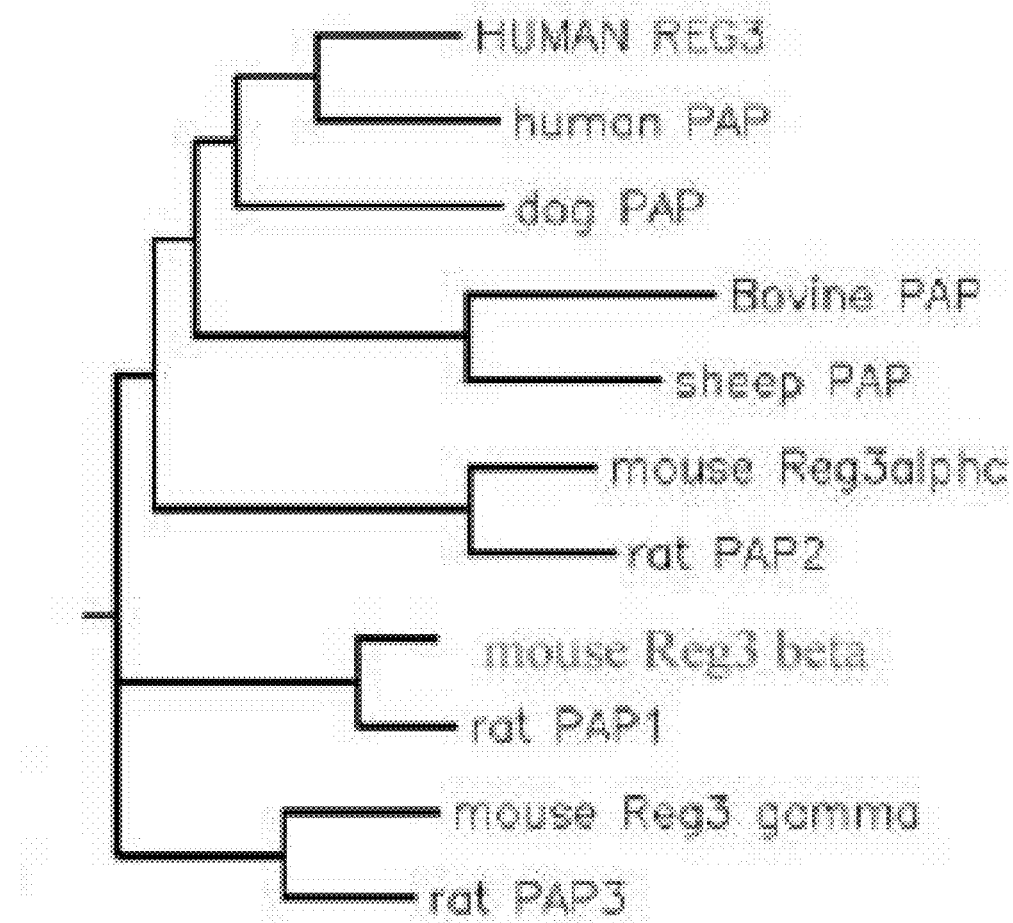
FIG. 1B depicts a phylogenetic analysis of PAP proteins from indicated species. Rat and mouse PAP clustered together, as did bovine and sheep PAP. Three subclusters were formed by rat and mouse PAP isoforms. Human and dog PAP did not cluster with any of the other PAP species.

To examine the relationship between PAP proteins across species, the amino acid sequences encoding rat, mouse, canine, sheep, bovine, and human PAP proteins were analyzed by multiple alignments using clustalW analysis (FIG. 1A). Depending on the species and isoform assessed, conservation of the primary structure for these proteins varied between 47 and 91%. This variation in the primary amino acid structure presumably permits various functions for these proteins. This is exemplified by the many diverse immunological functions that have previously been reported for select PAP isoforms. To further explore the relationship among these proteins, a phylogenetic tree was constructed for PAP (FIG. 1B). It should be noted that currently, three PAP isoforms are identified in mice and rats, two PAP isoforms are identified in humans, and one PAP isoform has been identified in canines, bovines, and sheep.

As shown in FIG. 1B, branching at the root suggests a common ancient origin. A large cluster was formed by mouse (Reg3α), rat (PAP2), sheep, bovine, dog, and human PAP. Interestingly, PAP isoforms from rodents formed their own independent clusters, with PAP1 clustering with Reg3β and PAP3 clustering with Reg3α. The final analysis reveals the greatest similarities exist between sheep and bovine PAP, mReg3α and rPAP2, mReg3β and rPAP1, mReg3γ and rPAP3, and the human Reg3/human PAP subcluster forming a cluster with canine PAP. This phylogenetic analysis shows that the PAP family is conserved across species but disparities exist as demonstrated by tighter clusters among the indicated PAP isoforms. Thus, these analyses reveal that several PAP isoforms are more closely related than others.

Structure and Domain Analysis of PAP Proteins

Primary sequence analysis of PAP proteins reveals there are two major domains that make up the entire protein. With the exception of a small N-terminal domain which will be referred to as the PAP domain, the vast majority of the protein consists of the C-type lectin domain. The PAP domain is an extremely hydrophilic region consisting of the first 13 aa of the protein (FIG. 1A, labeled (A)). Included within this region is a highly conserved trypsin cleavage site located at positions $Arg_{11}$-$Ile_{12}$ (FIG. 1A, double line). Studies show that trypsin cleavage of certain PAP isoforms generates highly insoluble fibril structures that are prone to precipitate. The biologic significance of this site in PAP proteins is not presently well understood. The C-type lectin domain within PAP stretches from residues 14-149. Classification of proteins as C-type lectins is based on key motifs and residues. Conserved C-type lectin residues found in PAP proteins are denoted with the bottom row of stars (FIG. 1A). Within the CRD domain of PAP proteins, several but not all C-type lectin motifs are conserved. Beginning with the N-terminal region of the CRD domain, residues 14-25 are less conserved motifs that are present only in long-form C-type lectin proteins (FIG. 1A, labeled (B)). These residues form a β-hairpin that is stabilized by two less conserved cysteines which form a disulfide bond. Invariant cysteine residues are located at positions 42, 120, 137, 145 (FIG. 1A, denoted by black dots).

The calcium-binding domain, "EPN" motif (positions 88-90), and glutamic acid (position 108) is present in all PAP proteins except rat PAP2 and mouse RegIIIα. The "WND" motif, also involved in calcium binding is absent in all PAP proteins. The highly conserved "WIGL" motif (residues 77-80) is present in all except for the PAP2 isoform, where the highly conserved glycine is replaced with a tryptophan residue, generating a WIWL sequence. The significance of this observation is presently not well understood.

Located on the C terminus of PAP proteins, between residues 120-149 (FIG. 1A, labeled (C), and FIG. 1A, Part 2) is the C-type consensus sequence, which is commonly used as a landmark for sequence analysis. The loop region, which is the variable part of all C-type lectins, is depicted by unlabeled black boxes in FIG. 1A. Assessment of the secondary architecture for PAP proteins using PELE analysis demonstrates these proteins all share a common secondary backbone—$β_1α_1β_2α_2β_3β_4β_5β_6β_7$—which is in accordance with the secondary structure of C-type lectins (FIG. 1A).

Analysis of PAP2 Tertiary Structure

The outline for mutational analysis of PAP2 is shown in FIG. 2A. Because of the strong primary sequence conservation within the PAP group of proteins, the Applicants used the homology recognition program PHYRE to construct a tertiary structure for rat PAP2 (FIG. 2B). PHYRE modeled the tertiary structure for PAP2 on the x-ray crystal structure of human PAP (the overall structure of PAP2 displays the prominent features that encompass the C-type lectin domain (CTLD) fold (1)). This includes the considerable conservation of hydrophobic residues involved in the formation of the hydrophobic core, two antiparallel β sheets, two α helices which flank each side of the structure, and three disulfide bonds.

Figure 2:
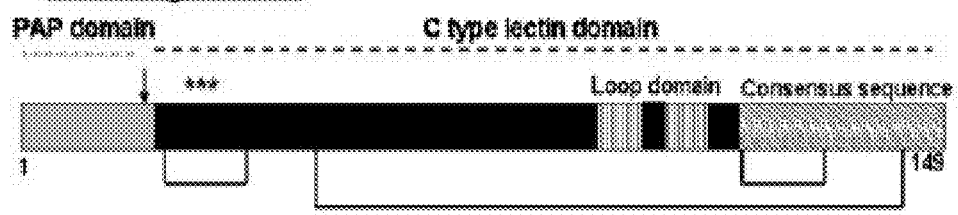
FIG. 2A depicts a schematic outline of domains within full-length PAP2 and mutants. The "PAP domain" is depicted on the N terminus with a small arrow indicating the location of the trypsin cleavage site. The long-form C-type lectin domain immediately follows the PAP domain, which is depicted by three asterisks (* * *) in the illustration. Within this location lies the less conserved disulfide bond. The long loop region is indicated by the striped area. The consensus sequence is located on the C terminus (horizontal lines). Three of the four invariant cysteines are found within the consensus sequence.
FIG. 2B depicts B the C-terminal truncated mutant. It is noted that deletion of the consensus sequence eliminates the last 30 residues, and two invariant disulfide bonds.
FIG. 2C depicts the N-terminal truncate mutant. Deletion of the first 25 residues removes the PAP domain and the long-form C-type lectin domain.
FIG. 2D depicts the predicted tertiary ribbon structure of PAP2, which was generated by the structural analysis program PHYRE. The PAP domain and the long-form domain are located on the lower half of the structure. The consensus sequence is highlighted in gray and the encoded secondary structures are labeled. Disulfide bonds are highlighted, with the invariant bonds depicted by the label (D). The loop region is located on the upper half of the structure, as indicated.
Figure 2:
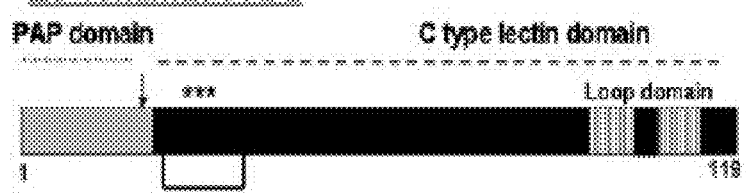
Figure 2:
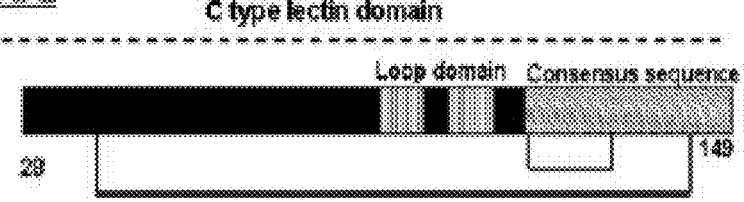
Figure 2D:
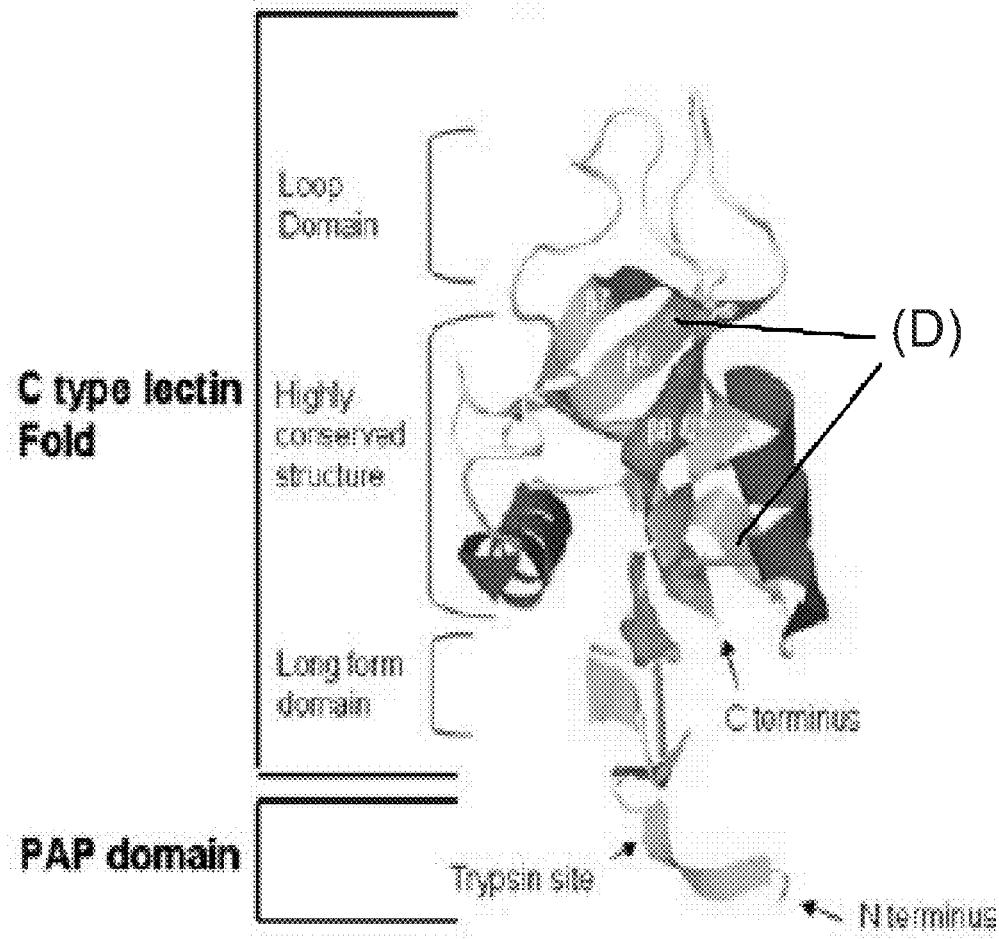

The loop region located on the upper half of the structure lacks secondary structures and exhibits variability in amino acid sequence. With respect to certain CTLD proteins, the loop region is commonly associated with calcium-dependent carbohydrate binding and protein binding. As shown in FIG. 2D, the PAP domain composes a small fraction of the entire complex and its location on the periphery of the overall complex demonstrates its independence from the Ctypelectin fold. Immediately following the PAP domain is the less conserved C-type lectin domain which is only found in long-form C-type lectins (FIG. 2A, and FIG. 1A, black boxed sequences). This region forms a small loop that contains two cysteines which form the least conserved disulfide bond.

The C-type lectin consensus region which corresponds to the last 29 residues is represented by the gray region in FIG. 2A-C. This region encompasses a significant part of the highly conserved C-type lectin fold segment of the tertiary structure. Additionally, as represented in FIG. 2B, the consensus sequence encodes for β sheets (β6, β7, β8) which are important for the formation of the two antiparallel β sheets. The entire upper antiparallel β sheet is formed by β6 and β7, and β8 pairs up with β1 to form the second antiparallel β sheet. Additionally, the consensus sequence contains three of the four invariant cysteines found in all C-type lectin proteins.

Mutational Characterization of PAP2 Domains

The Applicants have previously reported that rat PAP2 may be important for macrophage activity by specifically up-regulating the expression of IL-1, IL-6, and TNF-α. Due to its strong expression in acute pancreatitis, it is speculated that this isoform is an important modulator of the inflammatory process. To study the functional significance of regions of PAP2, the Applicants constructed truncated proteins and compared its activity with wild-type protein. Truncation studies were conducted on the PAP domain, the long-form C-type lectin region and the C-type lectin consensus sequence (FIG. 2). Truncation of the N-terminal domain of PAP2 (ΔN PAP2) containing the PAP domain and the C-type longform domain was found to be superfluous for the transcription and secretion of IL-1, IL-6, and TNF-α.

Figure 3:
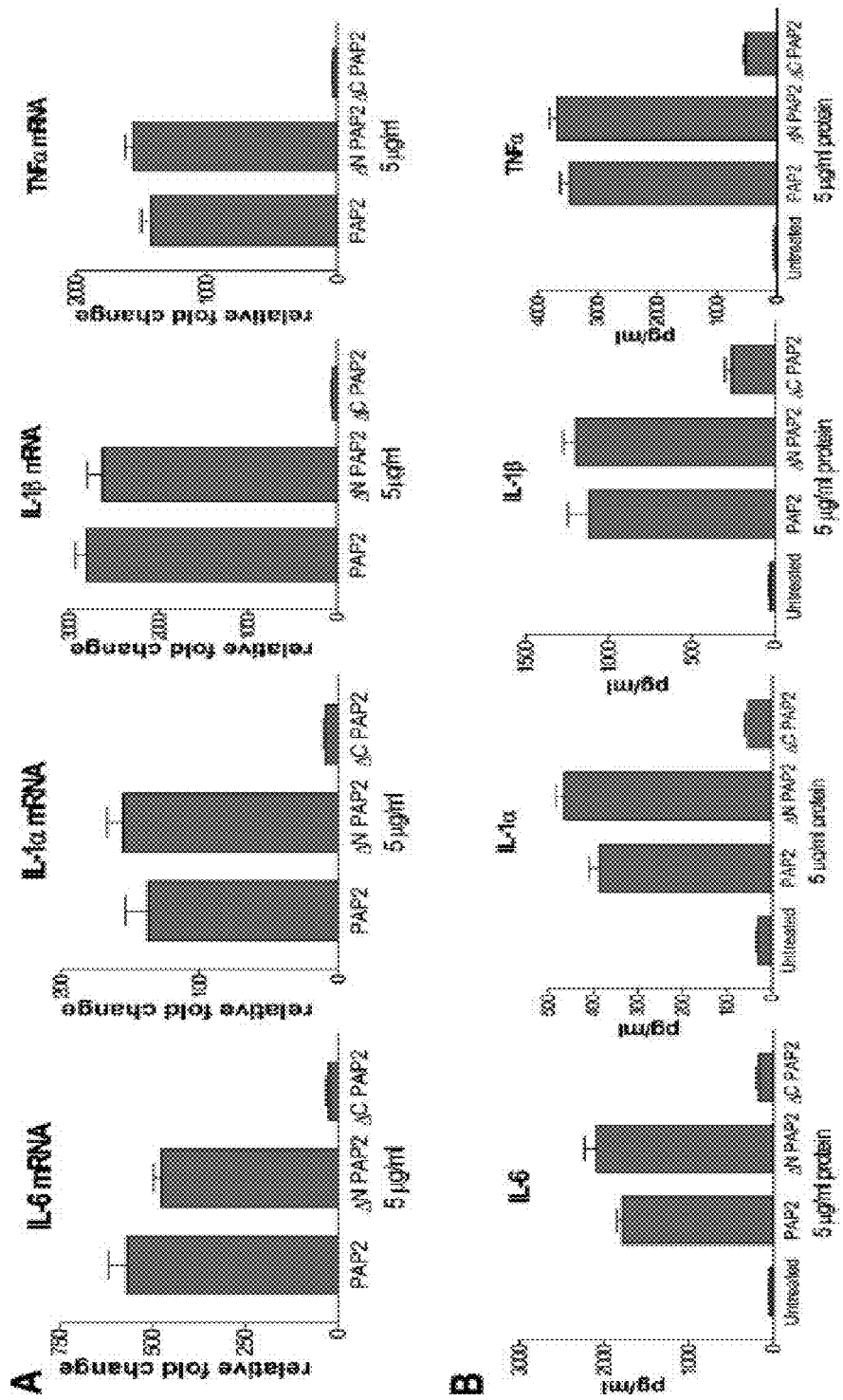
FIG. 3 depicts experimental results for the NR8383 cells cultured with 5 µg/ml of the specified protein for 24 h.

As depicted in FIG. 3A, total RNA was extracted from macrophages and subjected to one-step real-time PCR analysis for IL-1α, IL-1β, IL-6, TNF-α. The activity of the truncated mutants (ΔN PAP2, ΔC PAP2) was compared with full-length PAP2. There was no significant decrease in macrophage-derived cytokines after culturing with the N-terminal mutant. However, a significant decrease in activity was observed in the C-terminal mutant; p<0.05. B, Secreted cytokines were analyzed in the culture medium after administering recombinant proteins. Similar to the RNA analysis, the activity of ΔN PAP2 was comparable to full-length PAP2, whereas the activity of ΔC PAP2 was significantly less; p<0.05. As shown in FIG. 3, the activity of wild-type PAP2 and ΔN PAP2 on macrophage cytokine production and secretion was comparable. In contrast, truncation studies on the C-terminal consensus (ΔC PAP2) sequence completely abrogated the activity of PAP2 as demonstrated by basal levels of cytokine production by macrophages (FIG. 3). Unlike components of the N terminus, the C-terminal region of PAP2 is important for the function of PAP2. The PAP2 C-terminal truncation, amino acids 1-119, has the sequence listing:

(SEQ ID NO: 2)
EDSQKAVPSTRTSCPMGSKAYRSYCYTLVTTLKSWFQADLACQKRPSGHL

VSILSGGEASFVSSLVTGRVNNNQDIWIWLHDPTMGQQPNGGGWEWSNSD

VLNYLNWDGDPSSTVNRGN.

Disulfide Bond Analysis and Cysteine Mutations

Figure 4:
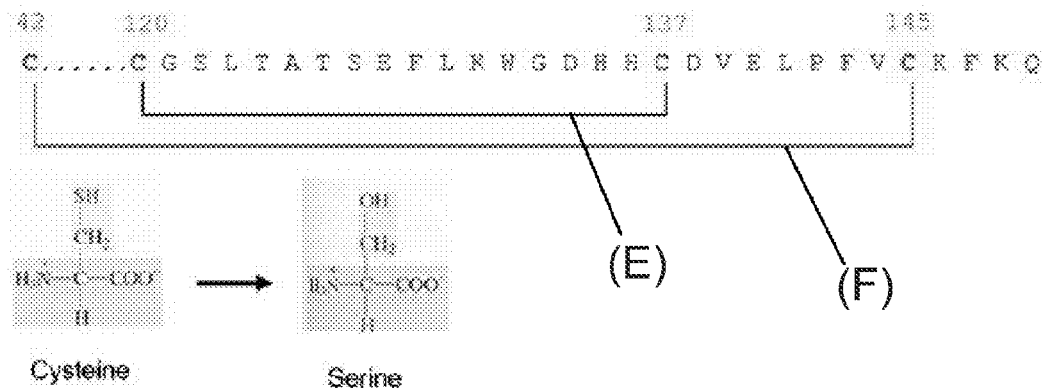
FIG. 4A depicts experimental results for the point mutations of cysteine residues in PAP2. Primary amino acid sequence illustrating the location and structural arrangement of the invariant cysteines. As depicted in by the bracket labeled (F)(Residues 15 . . . 93-122 of SEQ. ID. 1), cysteine 42 forms a disulfide bond with cysteine 145, whereas cysteine 120 pairs up with cysteine 137 (indicated by the bracket labeled (E) (Residues 90-110 of SEQ. ID. 1)). Point mutations were introduced for each cysteine residue. This consisted of a Cys3Ser substitution for $Cys^{42}$, $Cys^{120}$, $Cys^{137}$, $Cys^{145}$. Mutation of each disulfide bond was analyzed individually and concurrently.
FIG. 4B depicts the tertiary structure of PAP2 showing the location of the respected disulfide bonds. The bond formed by $Cys^{42}$-$Cys^{145}$ (indicated by the label (H)) stabilizes the coming together of the N and C terminus and the bond formed by $Cys^{120}$-$Cys^{137}$ (labeled (G)) stabilizes the upper loop domain.
FIG. 4C depicts the activity of recombinant mutant PAP2 proteins compared with full-length PAP2. NR8383 cells were cultured with 5 µg/ml of the indicated protein for 24 h followed by the analysis of TNF in culture medium. A significant decrease in activity was observed for all three mutants, $p<0.05$. Mutational analysis of the cysteines involved in the formation of the long-form disulfide bond did not affect protein activity (data not shown).
Figure 4:
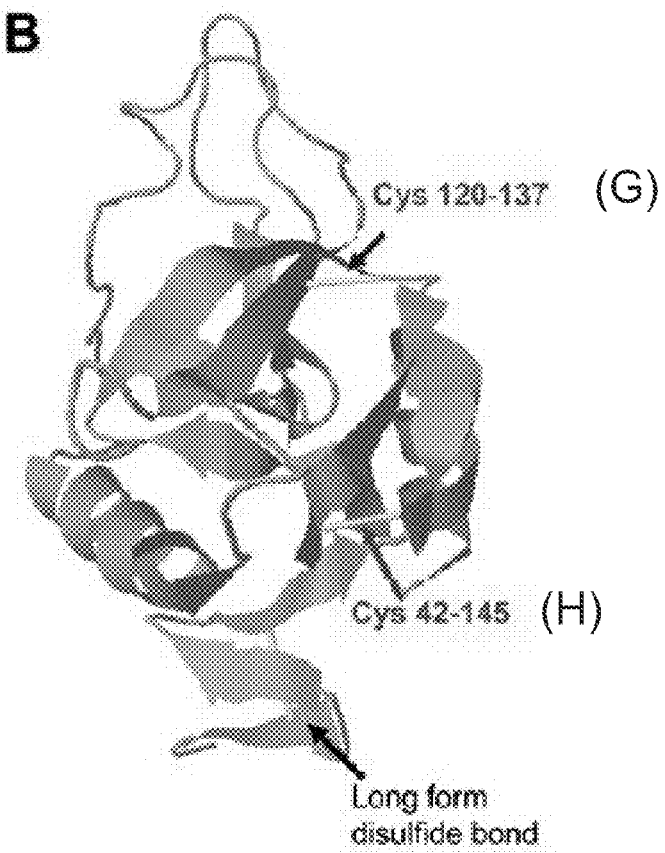
Figure 4C:
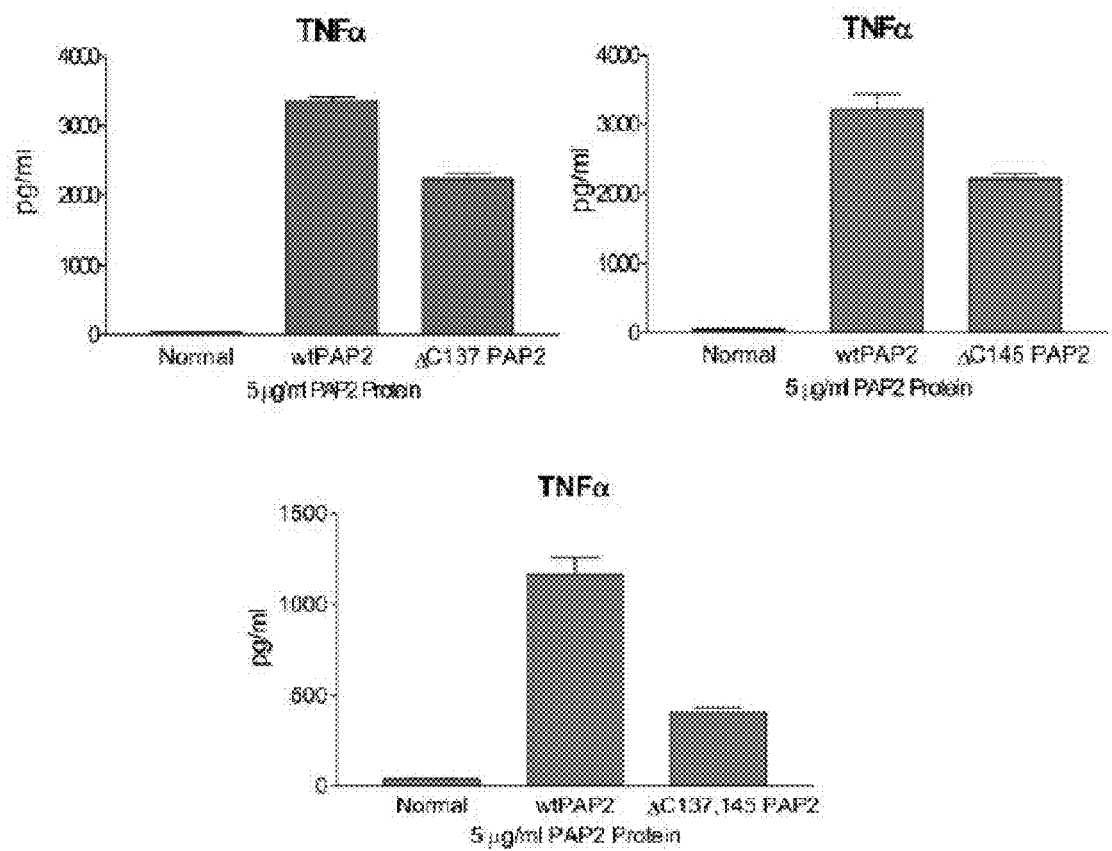
Figure 5:
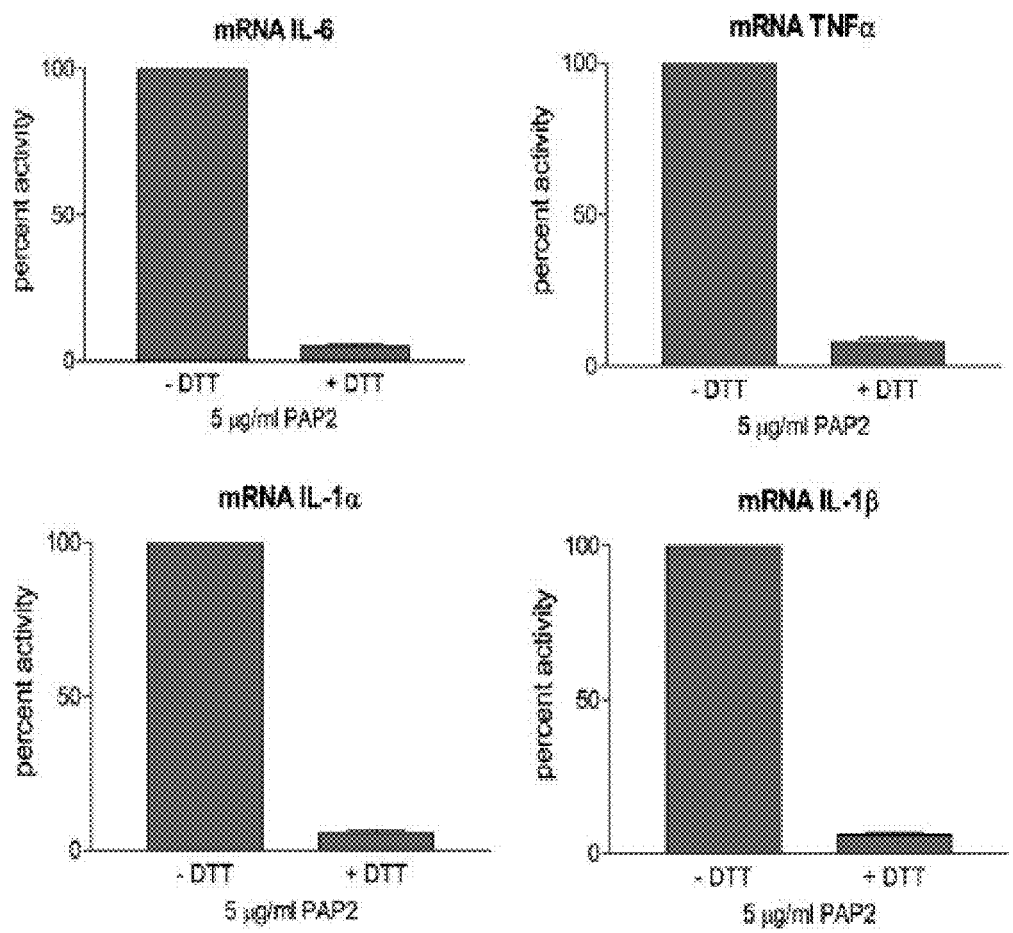
FIG. 5 depicts experimental results for the full-length PAP2 preincubated with 1 mM DTT for 1 h before culturing with NR8383 for 24 h. A significant decrease in PAP2 activity was observed as demonstrated by a decrease in the real-time analysis of IL-1α, IL-1β, IL-6, and TNF-α; $p<0.05$ for all four cytokines.

There are three intrachain disulfide bonds in PAP2 that are situated in different locations within its structure, and the primary amino acid sequence showing these locations is shown in FIG. 4A. Currently, the importance of these disulfide bonds is not known. Two of the three bonds correspond to the invariant disulfides present in all CTLDs (FIG. 1A, denoted by dots above cysteine residues). The less conserved disulfide bond, $Cys^{14}Cys^{25}$, is located within the long-form C-type lectin domain. The two invariant disulfide bonds, $Cys^{42}Cys^{145}$, are positioned on the lower half of the fold, whereas $Cys^{120}$-$Cys^{137}$ is present on the upper half of the fold (FIG. 4B). In the truncation studies, the importance of their disulfide bonds was indirectly assessed because cysteines involved in their formation were within the deleted sequences. Removal of the disulfide bond (ΔCys$^{120}$-Cys$^{137}$) that presumably stabilizes the upper region of the fold (loop region) resulted in an ~30-40% reduction in activity (FIG. 4C). Similarly, mutation of Cys$^{42}$ or Cys$^{145}$, thereby eliminating the bond located on the lower half of the fold, resulted in a 30-40% reduction in activity (FIG. 4C). Interestingly, the effects of double mutation studies removing both Cys$^{120}$-Cys$^{137}$ and Cys$^{42}$-Cys$^{145}$ disulfide bonds resulted in a 67% drop in activity (FIG. 4C). In FIG. 5, full-length PAP2 was subjected to the full reduction of its disulfide bonds (1 mm DTT at pH 8, 30° for 30 min) to provide sulfhydryl groups. Comparing the activity of reduced PAP2 with unmodified PAP2 on the secretion of inflammatory cytokines in macrophages revealed a significantly attenuated response in the reduced isoform. This result further indicates that disulfide bond formation is essential for the function of PAP2.

Effect of PAP2 Truncations/Mutations on Primary Macrophages

Figure 6:
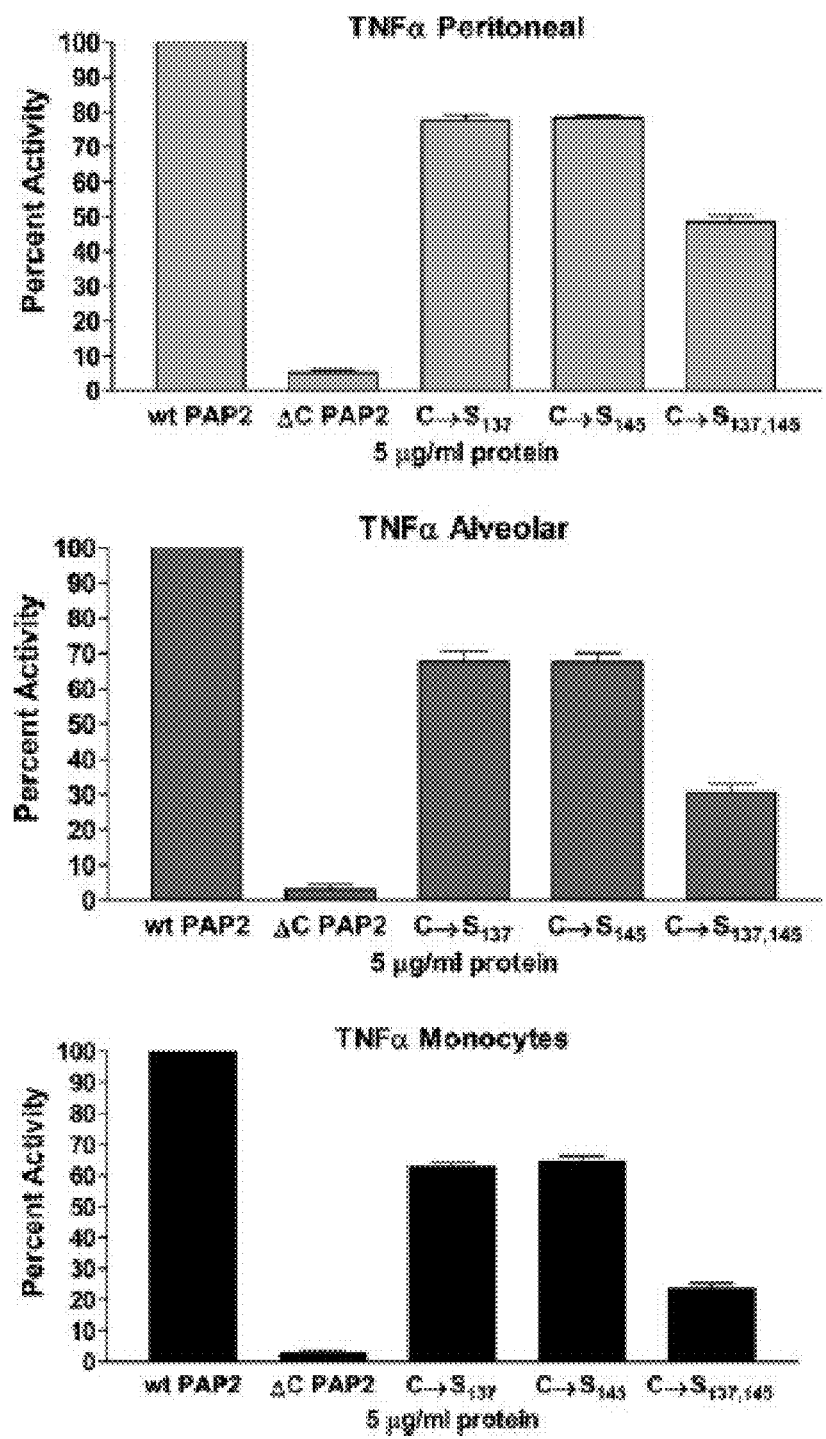
FIG. 6 depicts experimental results for the PAP assays on primary macrophages. Wild-type PAP2, ΔCPAP2, ΔC137 PAP2, Δ C145 PAP2, and ΔC137, 145 PAP2 were cultured with blood-derived monocytes and alveolar- or peritoneal-derived macrophages. Individual and concurrent point mutations demonstrated a decrease in TNF-α cytokine production compared with wild-type PAP2; $p<0.05$ for all primary cells tested.

The Applicants have previously demonstrated that PAP2 induces proinflammatory cytokine expression in both clonal macrophages (NR8383) and cells derived from primary sources, peritoneal, alveolar, splenic, and monocytes. In view of this, the effects of PAP-mutated proteins on macrophages obtained from primary sources were investigated. As shown in FIG. 6, full-length PAP2 induced TNF-α expression in primary macrophages. In contrast, ΔC PAP2 completely obviated TNF-α expression. Similar to the results obtained with the clonal cell line (NR8383), point mutations of ΔCys$^{14}$-Cys$^{25}$, ΔCys$^{120}$-Cys$^{137}$, and the double mutant ΔCys$^{14}$-Cys25 ΔCys$^{120}$-Cys$^{137}$ decreased TNF-α expression by 30-40% for the single disulfide bond mutants and 60-85% for the double disulfide bond mutant in all primary macrophages.

PAP2 Activates the NF-κB Pathway

Figure 7:
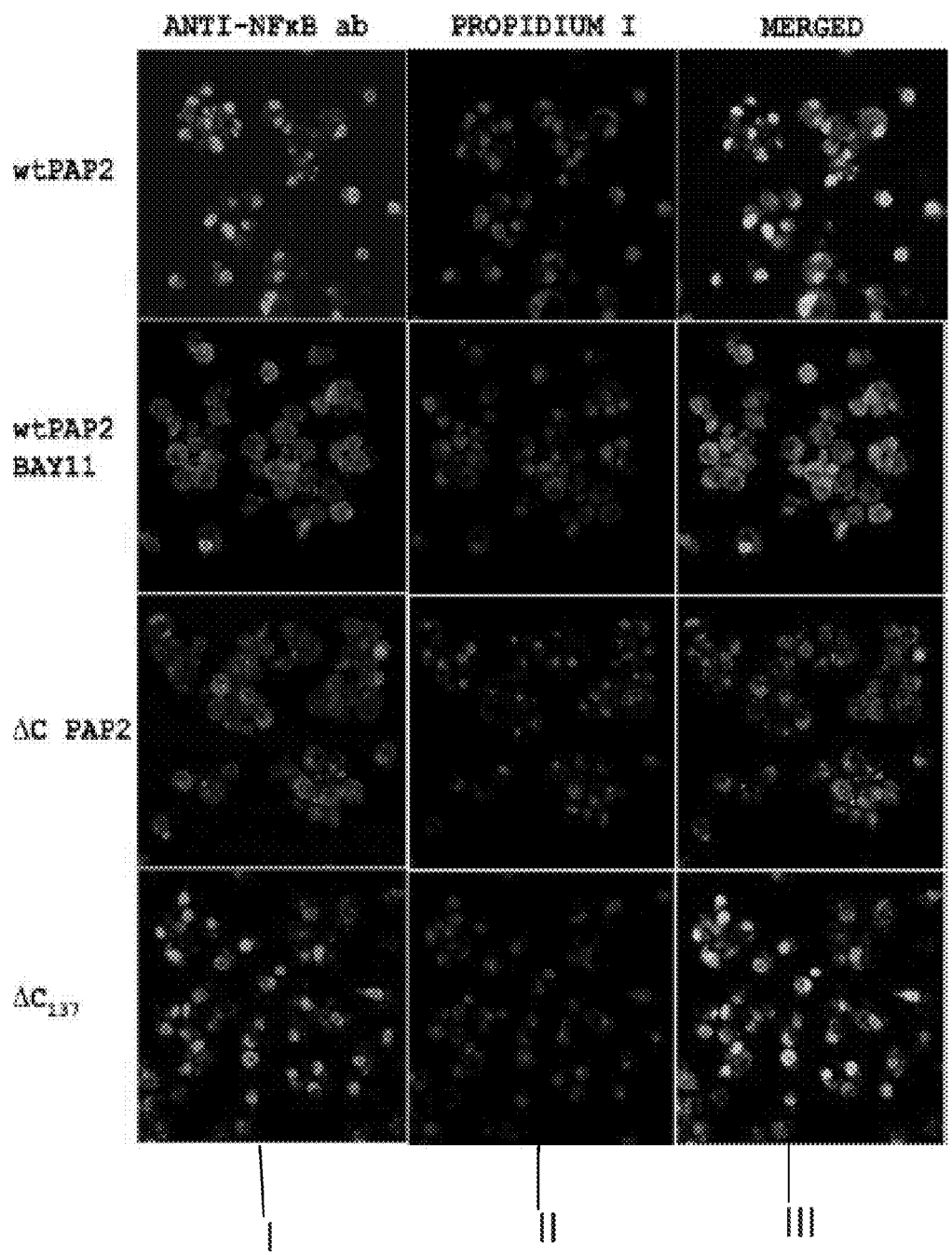
FIG. 7 depicts experimental results for the PAP2 mutational analysis of TNF-κB activation. NR8383 macrophages were cultured ±5 µg/ml wild-type or mutated PAP2 for 3 h and fixed with formaldehyde. Cells were subsequently stained with anti-NF-κB and propidium iodide and results are displayed individually or as merged images (confocal fluorescence microscopy). Data represent one of three experiments with similar results; *, $p<0.05$.

Previous studies have demonstrated that the NF-κB inhibitor Bay11 completely inhibited PAP2 mediated upregulation of inflammatory cytokines in macrophages. Building on this, the ability of mutated PAP2 to affect NF-κB-mediated translocation to the nucleus was investigated. As shown in FIG. 7, cells cultured with wild-type PAP demonstrate nuclear translocation whereas addition of NF-κB inhibitor Bay11 completely inhibited PAP2-mediated nuclear translocation. In contrast to wild-type, PAP cells cultured with ΔC PAP displayed a similar inhibition to that of NF-κB inhibition demonstrating the importance of the C terminus with respect to PAP activity. Interestingly, cells cultured with ΔC$^{137}$ demonstrated a reduction in nuclear translocation compared with wild-type PAP. Column I of FIG. 7 shows light portions (which were shown in the color green), Column II of FIG. 7 shows light portions representative of the color red, while Column III shows light portions as a merge of red and green. Similar results were obtained when cells were cultured with C$^{147}$ and greater reduction in nuclear translocation was observed with dual mutated (ΔC$^{137}$, ΔC$^{147}$) PAP (data not shown).

Results of Experimentation

Verification of PAP Expression

Figure 8:
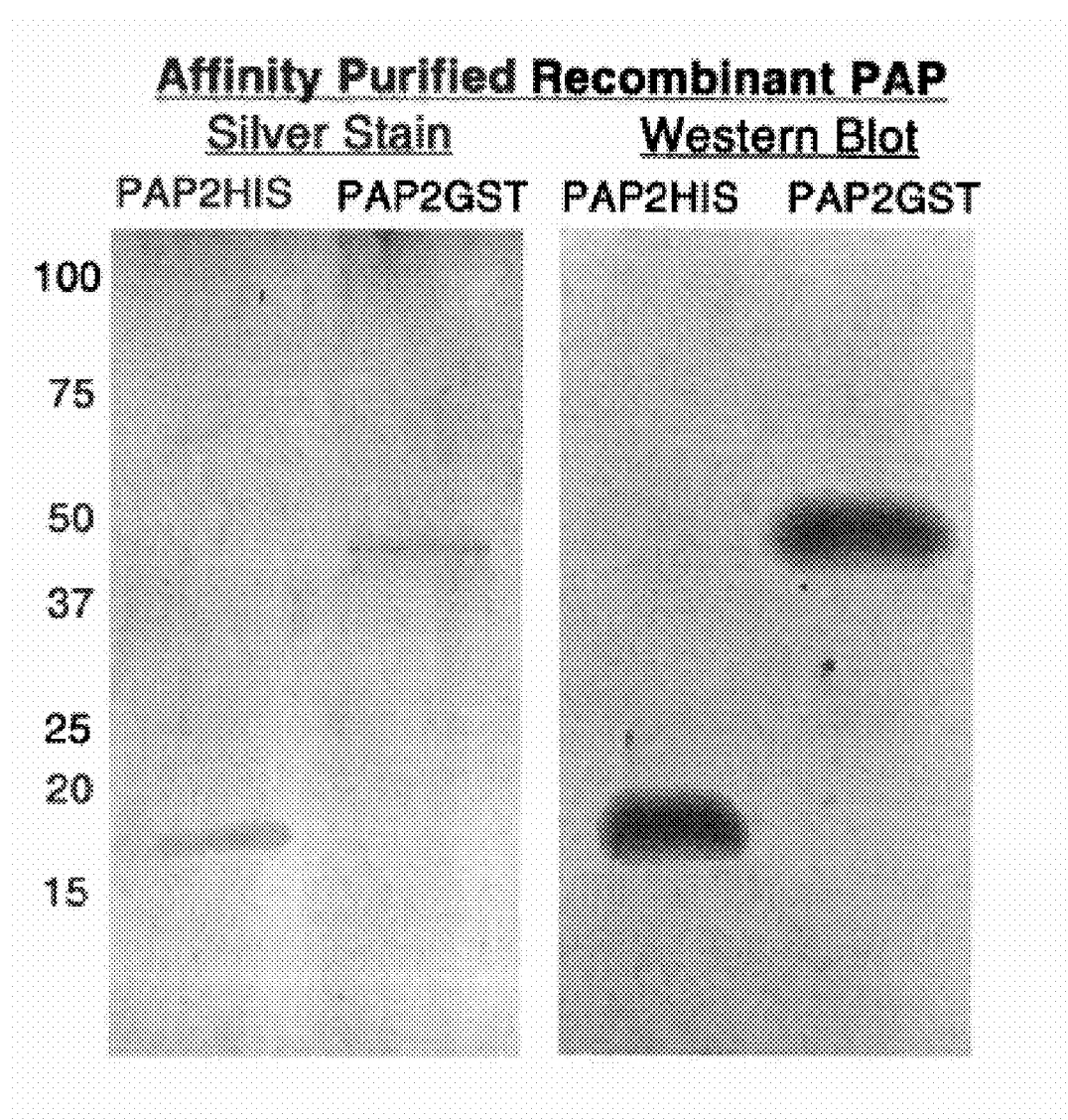
FIG. 8 depicts the characterization of GST and HIS tagged PAP. Affinity purified PAP2 proteins were loaded on a 15% SDS-polyacrylamide gel and stained with silver stain (left panel). Western blot of affinity purified proteins with a polyclonal PAP2 antibody (right panel). Recombinant PAP2 was generated with either an N terminal GST tag or a C terminal HIS tag.

The ability to generate different forms of recombinant PAP2 using the novel methods of the present invention was experimentally confirmed. As shown in FIG. 8, silver stain analysis demonstrated the presence of single bands at 43 kDa and 17 kDa MW which correspond to PAP-GST and PAP-HIS, respectively. Similarly these proteins were recognized by a specific PAP2 antibody demonstrating that the overlapping regions of both proteins are recognized and maintained. Final protein yields comprised of ~1.0 ug/ml for PAP2GST and ~0.4 ug/ml for PAP2HIS.

Comparing the Activity of PAP2HIS and PAP2GST

Figure 9:
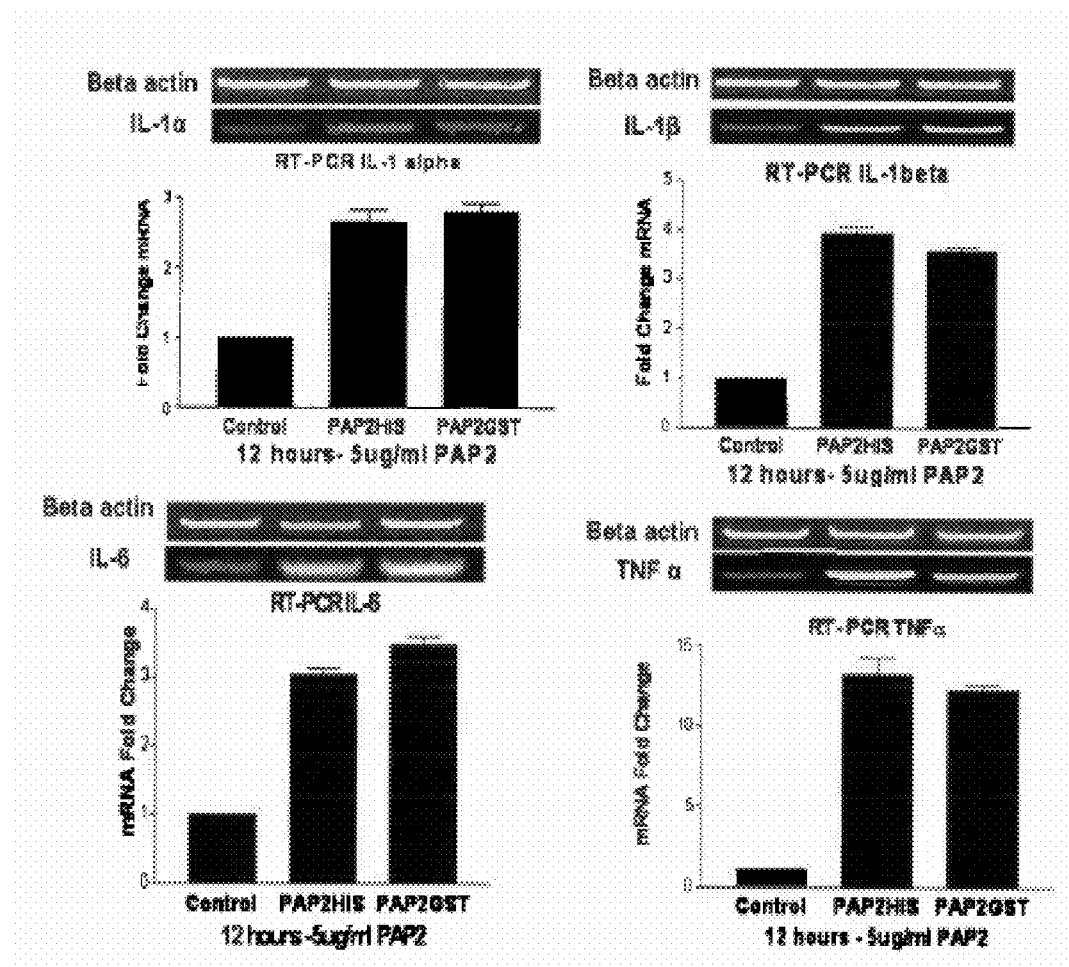
FIG. 9 depicts graphs which compare the protein activity for PAP2HIS and PAP2GST. Macrophages were cultured with equal amounts of each recombinant protein. Total RNA from control, PAP2HIS treated, and PAP2GST treated macrophages was subjected to RT-PCR. Using cytokine specific primers, the upregulation of IL-1α, IL-1β, IL-6, and TNF-α was assessed by PCR analysis and band intensity was quantitated on a 1% agarose gel utilizing the biorad system. Cytokines were standardized to beta actin. Treatment with both recombinant PAP proteins revealed relatively equal expression of the analyzed inflammatory cytokines. Beta actin control showed equal RNA loading.

Because PAP2 is considerably smaller (17 kDa) and linked to a larger GST protein (26 kDa), the possibility of a bulky GST component interfering with proper PAP2 activity or folding was considered. Therefore recombinant PAP2 with a smaller histidine tag was generated and its activity was compared to that of PAP2GST. Activity was assessed by analyzing for the upregulation of macrophage derived IL-1α, IL-1β, IL-6, and TNF-α after treatment with 5 ug/ml of PAP protein. As demonstrated in FIG. 9, semi-quantitative PCR revealed that there was a 3.6, 2.8, 13.0, 3.5 fold induction of IL-1α, IL-1β, TNFα and IL-6 after treatment with PAP2HIS and a 3.9, 2.6, 12.2, and 3.0 fold induction of IL-1α, IL-1β, TNFα and IL-6 after treatment with PAP2GST. This demonstrates that the functional capacity of PAP induced cytokine expression is maintained with both recombinant molecules and is not dependant on recombinant derivation.

PAP2 Mediates Bacterial Aggregation

Figure 10:
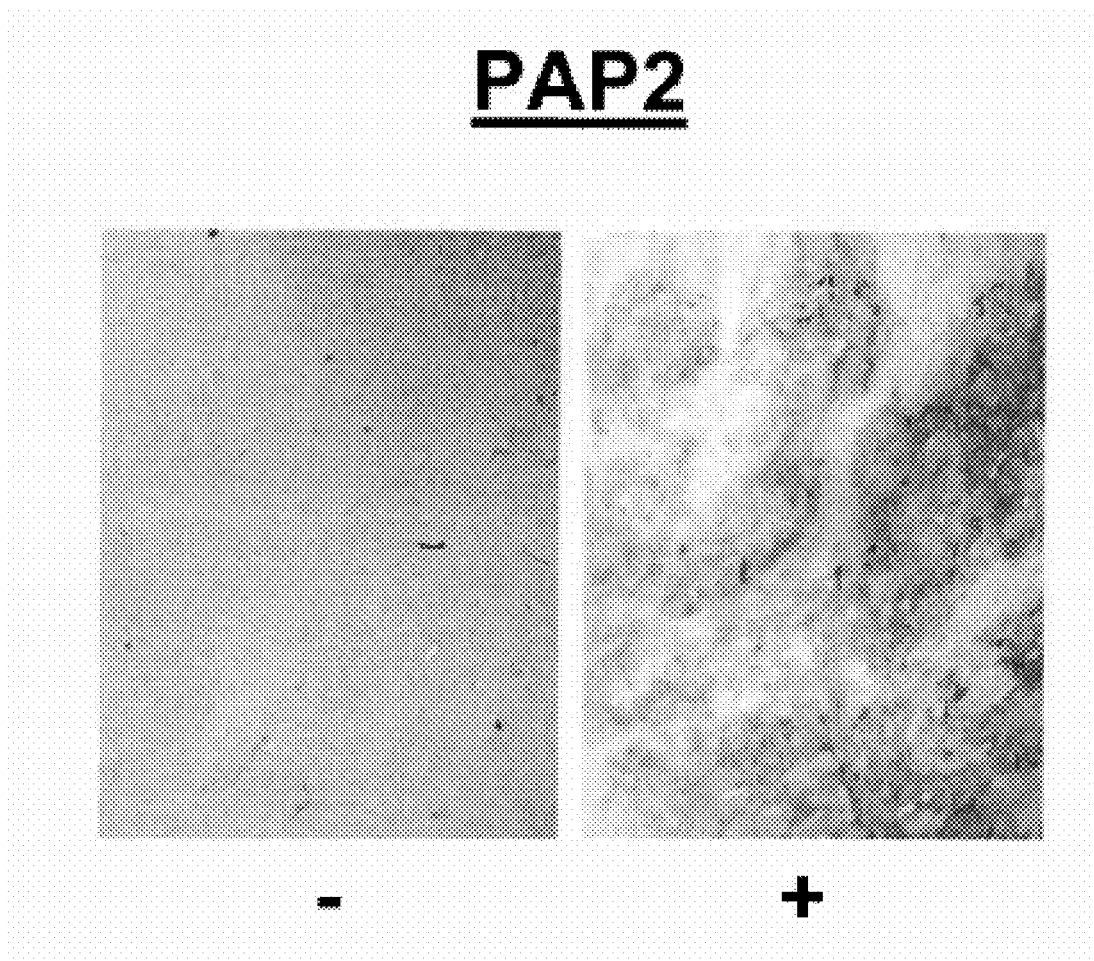
FIG. 10 depicts the experimental results when *E. coli* was incubated with either GST or PAP2GST for 1 h at 25° C. As demonstrated, increased bacterial agglutination is observed when cultured with PAP2GST protein. The GST control (left panel) did not result in bacterial agglutination.

Through their ability to bind to surface components on bacteria, many CTL proteins, such as mannose binding protein, are intrinsically involved in innate immunity. Previous studies have reported that PAP proteins are involved in the agglutination of both gram positive and gram negative bacteria. Bacterial agglutination by the PAP1 isoform was the first report to demonstrate an involvement in innate immunity. A study by Cash et al revealed that mouse Reg3γ and human PAP only recognize gram positive bacteria. Additionally, the Reg 1 protein, a distant relative of PAP proteins is able to bind and agglutinate both gram positive and negative bacteria. In this study, the ability of PAP2 to bind to *E. coli* was investigated. This was examined because PAP2 is the most abundant isoform in rats with experimental acute pancreatitis and gram negative bacteria is the most common infectious agent to pose a problem due to its presence in the gastrointestinal tract. As demonstrated in FIG. 10, incubation with recombinant PAP2 led to a time dependent increase in bacterial aggregates which was absent in controls. These data demonstrate that PAP2 may be integrally involved in the maintenance of bacterial growth and propagation in the setting of acute pancreatitis.

Analysis of C-Type Lectin Domains

Specific C-type lectin domains and residues were analyzed by mutational analysis and analyzed their capacity to support the expression and secretion of IL-1α, IL-1β, IL-6, and TNF-α from macrophages. Mutants were originally constructed that lacked residues 1-25 on its N terminus or residues 120-149 on its C terminus. To observe the significance of these domains on the proteins tertiary structure, a computer-generated model of PAP2 was used, which was created by PHYRE. This program modeled the structure of PAP2 based on the crystal structure of human PAP. In these findings, it was observed that the N-terminal deletion did not affect the activity of PAP2 whereas the C-terminal deletion significantly decreased the activity of PAP2. Then, a mutant that lacked the small N-terminal PAP domain (which is the only region that is not related to the C-type lectin domain) was constructed. When compared with full-length PAP, the activity of this mutant was comparable, thus retaining the ability to induce cytokine expression in macrophages. To further investigate this region of the protein, truncated studies were performed on the ensuing C-type lectin long-form domain. This domain contains two less conserved cysteines which are involved in the formation of the disulfide bond located in that region of the protein structure. Interestingly, it was observed that the combined deletion of the PAP domain and the long-form domain (residues 1-25) did not affect cytokine induction in macrophages. Thus, it was speculated that this part of the protein is not involved in the putative macrophage-binding domain.

Also, a C-terminal mutant that lacked the C-type lectin consensus sequence (residues 120-149) was constructed. Deletion of this region results in the removal of β sheets (β6, β7, β8). Analysis of the location and significance of these secondary structures within the proteins' tertiary structure suggests an important domain which may explain the observed response in macrophages. Thus, it was speculated that the loss of these critical secondary structural elements likely results in a gross structural instability in the tertiary structure of PAP2. Additionally, the truncation of this domain eliminates three invariant cysteine residues that are involved in the formation of two disulfide bonds: one stabilizes the upper fold and the other stabilizes the lower fold. Thus, because the truncation studies indirectly assessed the role of these disulfide bonds on the activity of PAP2, it was next decided to take a more direct approach.

As previously mentioned, there are three intrachain disulfide bonds in PAP2: one is located in the long-form domain and two correspond to invariant bonds associated with all C-type lectin proteins. These disulfide bonds were analyzed in the absence of any deleted structures, and it was observed that reduction of the cysteines with low concentrations of DTT resulted in an absolutely nonfunctional PAP2. Additionally, because the longform disulfide bond is located within the deleted N-terminal domain which did not have any inhibitory effect on protein activity, this bond is apparently not important for PAP2 activity. However, due to the arrangement and internal location of the invariant cysteines, it was speculated that the resulting disulfide bonds associated with these specific cysteines are most important for the overall structure and function of PAP2.

To test this hypothesis, site-directed mutagenesis of each individual cysteine was performed individually and sequentially. By generating a single point mutation that replaces a cysteine for a serine in rat PAP2, the Applicants demonstrated that the loss of $Cys^{42}$, $Cys^{120}$, $Cys^{137}$, and $Cys^{145}$ markedly impairs cytokine production in macrophages. Absence of the $Cys^{42}$-$Cys^{145}$ bond on the lower pole of the structure resulted in a 30-40% reduction in activity and the deletion of the $Cys^{120}$-$Cys^{137}$ bond on the upper half of the structure similarly resulted in a 30-40% reduction in activity. Moreover, double deletion of both invariant disulfide bonds resulted in a 70-80% drop in activity. These findings were observed in clonal and primary macrophages derived from blood, lung, and peritoneum. In contrast, point mutations of $Cys^{14}$ and $Cys^{25}$ did not alter the function of PAP2. This further edifies the hypothesis that the absence of these critical disulfide bonds most likely affects the ability of the protein to properly fold. Additionally, because PAP proteins are secreted, it appears that the highly stable disulfide bonds would make these proteins capable of withstanding harsh extracellular environment. The deletion of these disulfide bonds appears to make the protein more susceptible to harsh external factors including shifts in ionic strength, temperature, and pH.

Within select C-type lectin proteins, the loop region has been reported to be important for protein function including: carbohydrate binding, protein binding, and homodimerization. With reference to the C-type lectin expressed on NK cells, the loop region of the LY49 receptor interacts and binds to its ligand, the MHC class I receptor expressed on other cells. The loop region has also been shown to be important for the dimerization of C-type lectin snake venoms. For this reason, the functional role of the loop domain in PAP2 was analyzed. Interestingly, this region coincides with segments displaying higher variability in amino acid sequence among members of the PAP family. The PAP2 loop domain is divided into two independent loop regions that are separated by β-sheets β4 and β5. The first loop, which corresponds to residues 81-92, appears to be the less variable loop whereas increased variability can be appreciated in the second loop domain (residues 107-119). Interestingly, within the second loop, rat PAP2 and mouse Reg3α share 92% sequence identity. Because the loop region is a highly exposed area, the approach to studying this part of the protein included a classic Ab inhibition approach: polyclonal Abs were raised against residues 81-119. Intriguingly, it was observed that the incubation of full-length PAP2 with surplus polyclonal anti-PAP2 Ab did not attenuate the cytokine response in macrophages. This suggests that the loop region is not pertinent to PAP2-mediated induction of macrophage cytokines. However, it is plausible that the full inhibition of this region by Abs does not fully occur. Potential problems with the Ab-neutralization experiment include the way the Abs were designed. Because a partial protein sequence was expressed and used in the immunization process, it was speculated that it may be possible that the partial peptide did not fold according to the loop domain in full-length PAP2, thus giving rise to Abs that recognize a linear peptide sequence or irregular epitope. Thus, the purified Abs may not recognize the tertiary epitope that was originally set out to create.

onstrate a reduction of NF-κB nuclear translocation compared with wild-type PAP. These data demonstrate the importance of the C terminus and the disulfide bonds involved in PAP-mediated immunomodulatory function. The signaling of PAP proteins through the NF-κB pathway has been previously described for other PAP isoforms. PAP1 has been shown to be a negative regulator of this pathway in a rat model of inflammatory bowel disease. Similar results were observed for PAP1 in macrophages, and acinar cells. An in vivo rat study demonstrated that a high dose of PAP1 activates the NF-κB in hepatocytes. PAP activation of NF-κB was also found to be important for the survival of damaged motor neurons.

Thus, the Applicants' findings corroborate previous reports and are novel in the sense that activation of this pathway by PAP2 was demonstrated and that structural integrity of the disulfide bonds is vital for PAP2 activity.

In summary, this study on PAP2 provides the first structurally based analysis of a member of the PAP protein family. Through protein truncation studies, chemical analysis, and point mutation studies, the Applicants demonstrate that the reservation of the CTLD fold may be necessary for the function of PAP2 on macrophages. Moreover, deciphering potential biologic domains on PAP2 could have significant implications in designing therapies for diseases such as acute pancreatitis.

TABLE 1

| Percent homology of PAP protein across species | | | | | | | | | | | |
|---|---|---|---|---|---|---|---|---|---|---|---|
| | Rat PAP1 | Rat PAP2 | Rat PAP3 | Mouse RegIIIα | Mouse RegIIIβ | Mouse RegIIIγ | Human Reg3 | Human PAP | Canine PAP | Sheep PAP | Bovine PAP |
| Rat PAP1 | | 58 | 66 | 58 | 91 | 67 | 65 | 67 | 65 | 55 | 53 |
| Rat PAP2 | 58 | | 63 | 86 | 59 | 58 | 60 | 57 | 59 | 52 | 48 |
| Rat PAP3 | 66 | 63 | | 62 | 68 | 85 | 65 | 66 | 65 | 56 | 56 |
| Mouse RegIIIα | 58 | 86 | 62 | | 59 | 57 | 65 | 60 | 63 | 52 | 47 |
| Mouse RegIIIβ | 91 | 59 | 68 | 59 | | 71 | 67 | 67 | 63 | 58 | 53 |
| Mouse RegIIIγ | 67 | 58 | 85 | 57 | 71 | | 64 | 65 | 63 | 57 | 55 |
| Human Reg3 | 65 | 60 | 65 | 65 | 67 | 64 | | 83 | 76 | 63 | 61 |
| Human PAP | 67 | 57 | 66 | 60 | 67 | 65 | 83 | | 72 | 61 | 58 |
| Canine PAP | 65 | 59 | 65 | 63 | 63 | 63 | 76 | 72 | | 61 | 58 |
| Sheep PAP | 55 | 52 | 56 | 52 | 58 | 57 | 63 | 61 | 61 | | 78 |
| Bovine PAP | 53 | 48 | 56 | 47 | 53 | 55 | 61 | 58 | 58 | 78 | |

The Applicants have previously showed that PAP2-mediated up-regulation of inflammatory cytokines in macrophages was blocked by an inhibitor of the NF-κB pathway. In this report, it was demonstrated that PAP2 mediates the expression of the previously indicated cytokines through the NF-κB pathway. The translocation of p65 into the nucleus of macrophages after culturing with PAP2 is revealed by immunofluorescence. After a 2-h treatment with PAP2, over 75% of macrophages stain positively for nuclear NF-κB. Similar activation of the NF-κB pathway at these early time points has been reported. In contrast, treatment with C-truncated PAP reduced NF-κB nuclear translocation in a manner similar to that of NF-κB inhibition. Furthermore, PAP point mutation at the cysteine residues either individually or together also dem- In an attempt to assess the role of PAP2 the Applicants generated two recombinant versions of PAP2. Previous studies have demonstrated that PAP possesses immunomodulatory function in that it is able to affect macrophage morphology and induce expression of inflammatory cytokines in a dose dependent manner. Others have reported that PAP can serve as a chemoattractant for leukocytes, affect self expression and are capable of forming homodimers as well as heterodimers. Conceivably, as different members of the PAP family appear to have different biologic functions, cellular physiology may be dependent on the dominating isoform, and the resulting biologic effect may depend on the stoichiometric levels of all three isoforms, as well as PAP binding proteins. Additionally, the biological function of PAP proteins may depend on diverse aspects such as protein concentration, cell type, as well as tissue environment.

The generation of PAP through recombinant methodology can be difficult and function can differ based on the method employed. Previous studies have reported the generation of PAP isoforms using both prokaryotic and eukaryotic hosts. Furthermore, PAP expression and purification using a bacterial system have resulted in the accumulation of aggregated recombinant protein.

In contrast to those studies where PAP was renatured by arginine-assisted procedures and dialyzed into a final salt solution, the Applicants observed that HIS tagged rat PAP2 did not tolerate this and completely precipitated from solution. Purified soluble PAP2HIS was obtained by sequential dialysis with decreasing levels of urea. The final PAP2HIS obtained was in a salt solution which contained 0.7 M urea which does not interfere with biological assays. This can be safely assumed because the activity of this protein was compared to soluble GST tagged PAP2. The methodology included generating a soluble C terminal GST tagged PAP2 protein in E. coli expression systems. Expression of GST tagged PAP2 at 4° C. cultures with low concentrations of IPTG (0.1 mM IPTG) generated approximately 0.4 ug/ml of soluble protein.

However, tagging a protein with GST can pose problems. Indeed GST tagging adds an additional 26 kD to the protein. Since PAP has a molecular weight of ~17 kD the addition of a GST tag may compromise the proteins function by either sterically hindering the active site or affecting tertiary structure. Thus a His tagged version of the PAP2 protein was generated as a means to assess for these potential problems and to compare protein activity. However, it should be noted that the addition of His residues can facilitate unwanted effects as well. Addition of histidine residues facilitated additional cationic (nickel and zinc) binding which may affect inflammatory responses. For example zinc has been shown to be integral to certain cytokine responses in animals models of inflammatory disease and therefore the HIS tagged PAP molecule may have differentially affected cytokine responses when compared with GST tagged PAP in the present system.

Nonetheless this data show that the function of either form of recombinant PAP is not affected in the assays employed. This elucidates a few important characteristics of PAP. (1) PAP function may reside in the C terminal region of the molecule which would not be affected by a bulky GST residue (2) the tertiary structure of the active site of PAP is not affected by either method of recombinant generation, and (3) this allows for two different methods to study alteration of PAP protein such as truncations or deletions depending of protein design. In short, these methods provide another means to further elucidate PAP function which will allow for a better understanding of the role of PAP in acute pancreatitis and other inflammatory diseases.

Since these hosts are unable to carry out post translation modifications, such as glycosylation and phosphorylation, it could be that the function of PAP may differ in these contexts. Differences in the glycosylation status of Reg/PAP have been observed, which may be responsible for the differences in Reg/PAP migration which can range from 16-19 kD. Consistent residues of GlcNAc(beta 1-6)[Gal(beta 1-3)]GalNAc alpha—have been reported, which ranged in size from 4 to 9 sugar residues. In contrast, other studies indicate PAP proteins are not glycosylated. Whether or not the function of Reg or PAP is contingent on differences in glycosylation status is currently unknown.

Investigation of Protein Domains within the PAP2 Protein by Mutational Analysis

In this study, the Applicants investigated the importance of specific protein domains within the PAP2 protein by mutational analysis. An emphasis was placed on analyzing C-type lectin motifs, invariant cysteine residues, and a short N-terminal PAP domain which is speculated to be involved in the formation of fibril particles after trypsin modification. The biological significance of each of these domains was assessed by truncation analysis or site-directed mutagenesis. The activity of each mutant was determined in vitro by measuring the expression of cytokines from macrophages and comparing it to full-length PAP2. Because PAP2 activates the NF-κB-signaling pathway, here the affect of mutant PAP2 protein activity on this pathway was examined.

Cell Culture and NR8383 Macrophage PAP Assays

The rat macrophage cell line, NR8383, was obtained from the American Type Culture Collection. Cells were cultured in F-12K medium supplemented with 15% FCS at 5% $CO_2$ and 37° C. Before experimentation, macrophages were plated and grown to confluence. Experimental conditions included culturing cells with recombinant PAP2 for the specified time period followed by the analysis of culture medium for secreted inflammatory proteins. Unless stated, the dosage of 5 μg/ml for PAP2 was used in all experiments. This dosage was selected because this concentration corresponded to the lower half of the log phase of preliminary dose-response experiments performed on NR8383 cells. Disulfide bonds in PAP2 were reduced with 1 mM DTT for 1 h before administering to NR8383 macrophages. The activities of mutant proteins were compared with full-length PAP2 and were represented as percent active.

Site-Directed Mutagenesis

Full-length PAP2 was used as a template for site-directed mutagenesis experiments. Mutagenesis was performed using the Quickchange II Site—Directed Mutagenesis kit (Stratagene). Mutant primers were purchased from Integrated DNA Technologies (Table II below).

TABLE II

Primer Sets for Cysteine Mutations

| Cysteine | Primer Set |
|---|---|
| 42 | Forward: GTAACTCTGACGTACTGAATTATC (SEQ. ID. NO. 3)<br>Reverse: CTTAGTGGAGGTGAGGCTTCCTT (SEQ. ID. NO. 4) |
| 120 | Forward: TATCTCAACTGGGATGGGGATCC (SEQ. ID. NO. 5)<br>Reverse: TTCCTCTACTGTCAACCGTGGTAACTG (SEQ. ID. NO. 6) |
| 137 | Forward: GGAGACCATCACTCTGATGTGGAATTACC (SEQ. ID. NO. 7)<br>Reverse: GGTAATTCCACATCAGAGTGATGGTCTCC (SEQ. ID. NO. 8) |
| 145 | Forward: GGAATTACCTTTTGTCTCCAAGTTCAAGCAGTA (SEQ. ID. NO. 9)<br>Reverse: TACTGCTTGAACTTGGAGACAAAAGGTAATTCC (SEQ. ID. NO. 10) |

Polymerase chain reactions (PCRs) were performed using a MJ Research thermocycler. Cysteine to serine point mutations were generated for cysteines involved in the formation of the three disulfide bonds: the long-form disulfide bond ($Cys^{14}$-$Cys^{25}$), the lower half bond ($Cys^{42}$-$Cys^{145}$), and the loop stabilizing bond ($Cys^{120}$-$Cys^{137}$). Cysteines involved in the formation of each disulfide bond were mutated individually. Mutant cysteine templates were subsequently used for another series of site-directed mutagenesis to generate cysteine mutants that affected more than one disulfide bond.

Alignment and Construction of Phylogenetic Tree

The 10 members of the PAP family were aligned at the amino acid sequence level using ClustalW software. Sequences were obtained from Gen-Bank. A pairwise distance matrix was obtained by calculating the proportions of different amino acids. The matrix was then used to construct trees by the neighbor joining method.

NF-κB Nuclear Translocation

NF-κB nuclear translocation was quantified in NR8383 cells by visual fluorescent microscopy. Cells were plated onto cover slips to 70% confluence and cultured with 5 μg/ml PAP2His for 3 h. Cells were washed in PBS and fixed with 3.7% paraformaldehyde and permeabilized with 0.1% Triton X-100. Slides were blocked with 2% BSA for 30 min followed by incubation with 1/300 anti-NF-κB for 1 h and Alexa Fluor 555-conjugated secondary Ab (Molecular Probes). Preliminary data has demonstrated that second messenger signaling can be evaluated at this early time period. Fluorescence was assessed by a confocal laser microscope.

Production of rPAP2 and Mutants

Full-length histidine-tagged rPAP2 protein was purified following a similar protocol to the one described above. As used herein, the term "purified" refers to a substantially pure form of the protein, which may be about 90-100% homologous, and more preferably at least 95% homologous. Desirably, the protein is about 100% homologous. Briefly, wild-type PAP2 or mutants were subcloned into the pET24a expression plasmid and transformed into bacteria. An overnight culture of transformed BL21-DE3 cells was diluted with 500 ml of Terrific Broth containing 100 μg/ml kanamycin and grown at 37° C. to an OD600 of 2.0 and induced with 0.1 mM isopropyl-D-thiogalactoside for 3 h. The cells were pelleted, resuspended in resuspension buffer, and sonicated on ice. Bacterial lysate was repelleted and resuspended in wash buffer followed by solubilization buffer containing 6 M urea. Because the recombinant proteins were insoluble, they were purified using nickel-charged beads under denaturing conditions in resuspension buffer. The purified proteins were renatured in two dialysis steps: the first in 0.8M urea, 0.2M arginine, 300 mM NaCl, 30 mM Tris-HCl (pH 7.0), 10% glycerol and then in 0.8 M urea, 300 mM NaCl, 20 mM Tris (pH 7.5) for a minimum of 15 h.

Isolation of Primary Macrophages

Following nembutal anesthesia, primary macrophages were isolated from the indicated organ systems. In all purifications, cell viability was >95% as determined by trypan blue staining Macrophage cell morphology was examined by light microscopy. Macrophage function, as determined by NO production, was determined by LPS stimulation.

Peritoneal Macrophages.

Rat peritoneal macrophages were obtained by i.p. injection of 15 ml of cold Hank's buffer 4 days after i.p. injection of 10 ml of 4% thioglycolate as previously described. Macrophages were then cultured in 12-well tissue-culture plates. After 1 h of incubation, nonadherent cells were removed by washing three times with PBS. Adherent cells, consisting of 95% macrophages, were supplemented with fresh F-12K medium and incubated at 37° C. for 2 h before experimentation.

Alveolar Macrophages.

Rat alveolar macrophages were isolated from lung tissue by bronchoalveolar lavage as previously described. Lungs were lavaged three times via a tracheal cannula with 10 ml of cold HBSS. The lavage solution was centrifuged at 1500 rpm for 15 min and the cell pellet was resuspended in F-12K medium and plated in 12-well culture plates.

Monocytes.

Whole blood was obtained from rats and collected in EDTA containing tubes. Blood was diluted 1/3 with PBS and placed on a Ficoll—Hypaque gradient and centrifuged at 800 g for 15 min. The buffy coat was isolated and contaminating RBC were lysed with a hypotonic RBC lysis solution (ammonium chloride) for 10 min. Cells were centrifuged (1500 rpm for 15 min) and pellets were washed three times with PBS. Cells were resuspended in F-12K medium supplemented with 15% serum and allowed to adhere to 12-well tissue-culture plates for 1 h. Nonadherent cells were removed by washing three times with PBS. Adherent cells contained ~95% macrophages.

Quantitative Real-Time PCR

Total RNA was purified from NR8383 macrophages by TRIzol extraction. Real-time RT-PCR was performed using the TaqMan One-Step RT-PCR master mix kit (Applied Biosystems) and the Applied Biosystems 7500 Real-Time PCR system. A total of 100 ng of RNA was used for each real-time PCR. Amplification (40 cycles) was conducted in a 25 μl reaction, containing 2×PCR master mix (catalog no. 4309169; Applied Biosystems), RNA, enzyme, and primer and probe (catalog no. 4309169; Applied Biosystems). Primer and probes used to analyze for IL-1, IL-6, TNF-α, and β-actin expression are summarized in Table III below. Probes contained the reporter dye 6-FAM at the 5' end and Black Hole Quencher-1 at the 3' end. Gene expression was quantitated relative to β-actin; relative expression of the target gene was calculated as 2ΔddCt, where dCt is the difference between the Ct for the gene of interest and the threshold cycle for β-actin. In each experiment, the value of the relative expression of the control sample (untreated) was given a value of 1 and the expression of other treatments was plotted relative to the control.

TABLE III

Primer and Probe Sets for Cytokine Gene Expression

| Real-Time PCR | Primer and Probe Sets |
|---|---|
| IL-1 α | |
| Forward | AGCCCATGATTTAGAGACCAT (SEQ ID. NO 11) |
| Reverse | TGATGAACTCCTGCTTGACGAT (SEQ ID. NO 12) |
| Probe | CAGATCAGCACCTCACAGCTTCCAGAATAATT (SEQ ID. NO 13) |
| IL-1 β | |
| Forward | CCAAGCACCTTCTTTTCCTTCA (SEQ ID. NO 14) |
| Reverse | AGCCTGCAGTGCAGCTGTCTAA (SEQ ID. NO 15) |
| Probe | AGCCCGTCCTCTGTGACTCGTGGGATGA (SEQ ID. NO 16) |
| IL-6 | |
| Forward | TCCAAACTGGATATAACCAGGAAAT (SEQ ID. NO 17) |
| Reverse | TTGTCTTTCTTGTTATCTTGTAAGTTGTTCTT (SEQ ID. NO 18) |
| Probe | AATCTGCTCTGGTCTTCTGGAGTTCCGTTTCTA (SEQ ID. NO 19) |

TABLE III-continued

Primer and Probe Sets for Cytokine Gene Expression

Real-Time PCR Primer and Probe Sets

TNF-α

| | |
|---|---|
| Forward | GACCCTCACACTCAGATCATCTTCT (SEQ ID. NO 20) |
| Reverse | TTGTCTTTGAGATCCATGCCATT (SEQ ID. NO 21) |
| Probe | ACGTCGTAGCAAACCACCAAGCGGA (SEQ ID. NO 22) |

Cytokine ELISA

IL-1, IL-6, TNF-α, and IL-10 were measured in tissue-culture medium by respective ELISA kits (R&D Systems) in accordance with the manufacturer's recommendations. The ELISA for these cytokines were sensitive to 50 pg/ml of the respective recombinant cytokine. Unless stated, all cytokine assays were performed after treatment with 5 µg/ml rPAP2 for 24 h.

Immunoblot Assay

NR8383 cells were stimulated with 5 ug/ml PAP2HIS for 5, 15, 30, 60, 120, 180 min. After the indicated times, cells were washed once with PBS, scraped, pelleted and resuspended in protein extraction buffer (RIPA buffer: 150 mM NaCl, 10 mM Tris pH 7.0, 0.1% SDS, 1.0% Triton X-100, 5 mM EDTA) and incubated on ice for 15 min. Lysates were centrifuged at 15,000 g for 20 min at 4° C., supernatants were collected for immunoblots. Protein concentrations were determined using the modified Lowry assay. Samples were placed on a 10% SDS PAGE followed by transfer onto nitrocellulose paper. The membrane was blocked with 2% BSA and probed with polyclonal Ab against P-IkB, total IkB, and P-JNK. Primary Abs were detected with a HRP-conjugated anti-rabbit polyclonal Ab, which was visualized using the Supersignal West Pico Chemiluminescent Substrate kit (Pierce Cat# 34080) and film.

Preparation of Recombinant PAP2GST

Recombinant PAP2GST was produced and purified from a bacterial expression system as follows: Total RNA was isolated from inflamed pancreas using the Trizol extraction protocol (Sigma, St. Louis, Mo.). A cDNA library was reverse transcribed from the purified RNA with the Ambion reverse transcriptase kit (Ambion, Austin Tex.). Full length PAP2 was PCR amplified from the cDNA library with the pfu turbo DNA polymerase (Strategene. La Jolla, Calif.) and digested with Xho/EcoRI restriction enzymes. For cloning purposes, each primer was engineered with a restriction site incorporated into its sequence. Forward primer-5' agc aga att cgaa-gactcccagaaggcagtgccctctacacg '3 (SEQ ID. NO. 23) and reverse primer-5' ctc act cga ggt cta ctg ctt gaa ctt gca gac aaa agg taa ttc cac atc '3 (SEQ ID. NO. 24). Digested PAP2 PCR amplicons were inserted in-frame into the PGEX-5x-1 (Amersham Pharmacia biotech, Piscataway, N.J.) bacterial expression vector as a Xho/EcoRI subcloning. E. coli strain DH5α was used to generate the plasmid construct. Purified constructs were sequenced for verification (GENEWIZ, South Plainfield, N.J.) and transformed into E. coli BL21 protein expression cells by calcium chloride transformation protocol. Positive clones were selected from ampicillin agar selection plates and grown overnight in 25 ml of LB-amp broth at 37° C. The following morning the culture was diluted into 500 ml of TB-amp broth, grown to a density of 2.0 OD, followed by induction with 500 ul of 0.1 mM isopropyl-D-thiogalactoside (IPTG) for two hours at 4° C. Bacteria was pelleted at 5000 rpm for 15 minutes and resuspended in resuspension buffer (300 mM NaCl, 20 mM Tris pH 7.5, 0.5% triton, 2 mM dithiothreitol) containing protease inhibitors (1 mM PMSF) and sonicated on ice. Lysates were centrifuged at 12,000 rpm for 15 min and supernatant containing soluble PAP2GST were batch incubated with glutathione sepharose beads (Amersham) for 3 hours.

After binding, sepharose beads were washed 10× with wash buffer (300 mM NaCl, 20 mM Tris pH 7.5, 0.5% triton, 2 mM dithiothreitol, 5 mM reduced glutathione) and eluted with 5 ml elution buffer (100 mM reduced glutathione, 500 mM NaCl, 20 mM Tris pH 7.5, 2.0 mM dithiothreitol) for 3 h on end over end rotator. Eluted proteins were placed in dialysis tubing (Spectra/Por Membrane 12-14,000 MW) and dialyzed in dialysis buffer (300 mM NaCl, 20 mM Tris pH7.5) for 10 hours. This was repeated 2 times. To eliminate the possibility of contaminating endotoxins, proteins were incubated with polymyxin beads for 30 minutes (Bio-Rad laboratories, Hercules Calif.). In addition, the final purified recombinant proteins were subjected to boiling prior to culture. LPS content of the purified samples was tested using the E TOXATE kits (Sigma Aldrich) and found to be less than 30 pg/ml. Control GST protein was induced and purified in a similar fashion.

Preparation of Recombinant PAP2HIS

In light of the possibility that the large GST tag could affect the activity of PAP2, as explained above, the Applicants generated a recombinant PAP2 with a smaller 6× histidine tag. As described earlier for PAP-GST construction, PAP2 amplicons were inserted in-frame into the pET24a bacterial expression vector (Novagen, San Diego, Calif.). Positive clones were transformed into BL21 (DE3) E. coli, grown to a density of 2.0 OD in 500 mls of TB broth and induced for three hours at 37° C. with 500 ul 2 mM IPTG. Bacteria was centrifuged and resuspended in resuspension buffer (300 mM NaCl, 20 mM Tris pH 7.5, 1.5% triton, 5 mM dithiotreitol) containing 1 mM PMSF protease inhibitor and sonicated on ice. Because PAP2HIS is found in inclusion bodies, the soluble bacterial lysate was disposed and the bacterial pellet was sequentially washed with wash buffer A (1.5% triton, 300 mM NaCl), pelleted at 12,000 rpm for 15 min and followed with resuspension in wash buffer B (1M UREA, 1.5% triton, 500 mM NaCl). Because PAP2HIS formed inclusion bodies, the bacterial pellet was resolubilized in 30 mls of resuspension buffer (6M UREA, 500 mM NaCl, 20 mM Tris pH 7.5, 5 mM dithiothreitol) for 1 hour.

Solubilized proteins were collected after centrifugation and placed over a G50 size exclusion chromatography column and 2 ml fractions were collected and analyzed by SDS PAGE. Samples containing abundant PAP2 protein were combined and batch purified with 1.5 mls bed volume of SP Sepharose Fast Flow cation exchange beads (Sigma Aldrich, St. Louis, Mo.) for 2 hours. Beads were washed and batch eluted with 15 ml elution buffer 1 (2M NaCl, 6M UREA) for 3 h and dialyzed in dialysis buffer (6M UREA, 500 mM NaCl, 20 mM Tris pH 7.5, 30 mM Imidazole) for 6 hours. The dialyzed PAP2 was then bound to 1 ml bed volume of nickel beads for 2 hours and eluted with 5 ml of elution buffer 2 (6M UREA, 500 mM NaCl, 20 mM Tris pH 7.5, 250 mM Imidazole, 10 mM EDTA). Eluted protein was dialyzed in refolding buffer (0.8 M UREA, 0.2 M arginine, 300 mM NaCl, 30 mM Tris-HCL pH 7.0, 10% glycerol) for a minimum of 12 h followed by dialysis in dialysis buffer (0.8 M UREA, 300 mM NaCl, 20 mM Tris pH 7.5) for 12 h which was repeated 2 times.

For both PAP-GST and PAP-HIS proteins, in order to eliminate the possibility of contaminating endotoxins, proteins were incubated with polymyxin beads for 30 minutes. Protein concentration was determined by bradford assay and confirmatory SDS PAGE coomassie stain. Similarly to ensure endotoxin free purifications, recombinant proteins were boiled at 95° C. for 15 min prior to macrophage studies. Additionally, LPS content of the purified samples was tested using the E TOXATE kits (Sigma) and found to be less than 30 pg/ml. Viability was always greater than 90% when macrophages were cultured in the presence of GST or HIS-PAP at all concentrations tested as demonstrated by trypan blue exclusion dye.

Detection of Recombinant PAP Proteins

Affinity purified proteins were boiled in SDS sample buffer for 5 min followed by loading onto a 15% SDS-PAGE gel. Subsequently, gels were either silver stained or transferred to nitrocellulose paper for western blot analysis.

Silver Stain Method:

All silver stain reagents were obtained from Bio-Rad and followed according to the manufactures recommendation. Gels were fixed in fixative buffer 1 (40% ethanol, 10% acetic acid) for 30 min, followed by two 15 min incubations in fixative buffer 2 (10% ethanol, 5% acetic acid). Following sensitization in oxidizer (0.02% sodium thiosulfate) for 3 min, the gels were extensively rinsed in deionized water and incubated in silver reagent (0.02% silver nitrate) for 15 min. Gels were rinsed in deionized water and incubated in developer for approximately 5 min. The reaction was stopped with 5% acetic acid.

Western Blot Method:

Following the transfer of recombinant proteins onto nitrocellulose paper, the blot was incubated in TSB blocking buffer (0.5% BSA, 150 mM NaCl, 10 mM Tris pH 7.5) for 30 minutes. Recombinant PAP2 proteins were detected using a polyclonal rabbit anti-rat PAP2 antibody (1:400) that is specific to the hydrophilic region of PAP2 protein sequence (TMGQQPNGGGWEWSNSDVLNYLNWDGDPSST) (SEQ ID. NO. 25). Blots were rinsed with wash buffer (10 mM Tris pH 7.5, 150 mM NaCl, 0.1% tween-20) three times for 15 min followed with a HRP-conjugated goat anti-rabbit IgG secondary antibody (1:20,000) for 1 h. Wash was repeated, three times for 15 min. Proteins were visualized using SuperSignal West Pico Chemiluminescent kit (Pierce, Rockford, Ill.) and exposed to film.

Anti-PAPII Antibody:

Polyclonal anti-PAP2 antibody was similarly obtained after injection of a 31 a.a. PAP oligo peptide protein sequence (TMGQQPNGGGWEWSNSDVLNYLNWDGDPSST) (SEQ ID. NO. 25) into rabbit (Cocalico Biologicals Inc, Reamstown, Pa.). This sequence represents a hydrophilic region of PAPII and is distinct from Reg I. The gene sequence coding for this protein was directionally cloned into PGEX-5X-1 plasmid (Amersham Biosciences/GE Healthcare, Piscataway, N.J.) using primer EcoRI (F-agcagaattc gaagactc-ccagaaggcagtgccctctacacg) (SEQ. ID. NO. 26) and XhoI (R-ctcactcgag gtc tac tgc ttg aac ttg cag aca aaa ggt aat tcc aca tc) (SEQ. ID. NO. 27) linked sequences generating a PAPII-GST fusion protein. Recombinant plasmids were transformed into BL21 competent cells (Stratagene, La Jolla, Calif.) and purified protein was obtained by glutathione column affinity chromatography.

PAP2 peptide used to generate anti-PAP2 antibody was generated by the Alignment Program within The ExPASy (Expert Protein Analysis System) software. Reg isoforms were compared and sequence homology obtained. Subsequent analysis demonstrated a unique amino acid sequence which had minimal overlap with other Reg isoforms. As shown in Table IV below, this oligopeptide contains ~20% homology to Reg I. This distinction allows for analysis of antibody-mediated neutralization of individual Reg proteins with minimal overlap; cross reactivity was not observed (data not shown).

TABLE IV

| | |
|---|---|
| Translated PAP2 Sequence | EDSQKAVPSTRTSCP(Met)GSKAYRSYCYTLVTTLKSW FQADLACQKRPSGHLVSILSGGEASFVSSLVTGRVNNNQ DIWIWLHDPTMGQQPNGGGWEWSNSDVLNYLNWDGDPSS TVNRGNCGSLTATSEFLKWGDHHCDVELPFVCKFKQ (SEQ ID. NO. 28) |
| Peptide Sequence Used to Generate anti-PAP2 Antibody | TMGQQPNGGGWEWSNSDVLNYLNWDGDPSST (SEQ ID. NO. 29) |
| Rat PAP2 Peptide | TMGQQPNGGGWEWSNSDVLNYLNWDGDPSS (SEQ ID. NO. 30) |
| Rat Reg1 Sequence | GLHDPKNNRRWHWSSGSLFLYKSWDTGYPNN (SEQ ID. NO. 31) |

Semi-Quantitative Cytokine Expression Analysis

NR8383 macrophages were grown to near confluence in 12 well plates and cultured with 5 µg/ml of recombinant PAP2GST for 3, 12, and 24 h. Total RNA was extracted from cultures with TRIzol (Invitrogen Life Technologies, Carlsbad, Calif.), quantitated by spectrophotometric measurement of absorbance at 260 nm and analyzed on a 1% agarose gel for quality. Purified RNA was treated with DNase free (Ambion) for 1 h followed by cDNA synthesis using the RETROscript reverse transcriptase kit (Ambion) according to the manufacturer's recommendations. Cytokines analyzed included IL-1α, IL-1β, IL-6, and TNFα. Cytokine expression was determined by standard PCR, utilizing 1 µl cDNA per reaction. PCR reactions consisted of 50 µl reactions that included 2.5 U of TaqDNA polymerase, 1× Taq buffer, 1 mM MgCl, 1 mM dNTPs and 1 µM of each specific primer (Table V below). PCR products were analyzed on a 2% agarose gel that was stained with ethidium bromide (500 ng/ml), and photographed. Gel bands were scanned by the Geldoc system 2000 and quantitated using the Quantity One software (Bio-Rad). Bands were quantitated based on band density.

TABLE V

Primer sets for cytokine gene expression

| Gene | Forward Primer | Reverse Primer |
|---|---|---|
| IL-1α | GTTCCTGACTTGTTTGAAGA (SEQ ID. NO. 32) | GATATCTGGAAATCTATCAT (SEQ ID. NO. 33) |
| IL-1β | TGAACTCAACTGTGAAATAG (SEQ ID. NO. 34) | CCATTGCTGTTTCCTAGGAA (SEQ ID. NO. 35) |
| IL-6 | CCGGAGAGGAGACTTCACAG (SEQ ID. NO. 36) | GAGCATTGGAAGTTGGGGTA (SEQ ID. NO. 37) |
| TNFα | ACTGAACTTCGGGGTGATCG (SEQ ID. NO. 38) | GTGGTGAGGAGCACATAGT (SEQ ID. NO. 39) |
| B-actin | GGCATTGTCACCAACTGGGA (SEQ ID. NO. 40) | ATCGTACTCCTGCTTGCTGA (SEQ ID. NO. 41) |

PAP2 Binds to Gram Negative Bacteria

*Escherichia coli* strain 25922 was obtained from the American tissue culture collection (ATCC). Briefly, bacteria was grown overnight in LB broth from a frozen stock. The following day, the bacterial culture was diluted 1:1 followed by plating onto a petri dish. Bacterial plates were incubated with either PBS or 5 ug/ml recombinant PAP2HIS or PAP2GST and placed on shaker for 1 h at 25° C. The aggregates were observed under a microscope.

Statistical Analysis

All data represent a minimum of 3 independent experiments and are expressed as the mean standard error (±SEM). Statistical analysis was performed using a 2-tailed Student t test or chi-square test. A P value of <0.05 was considered as statistically significant.

Information and procedures related to the present invention described above may be found in the following publications, each of which is incorporated by reference herein in its entirety: (1) Viterbo et al., "Mutational Characterization of Pancreatitis-Associated Protein 2 Domains Involved in Mediating Cytokine Secretion in Macrophages and the NF-κB Pathway", *Journal of Immunology*, 2008, 181: 1959-1968; (2) Lin et al., "Small-Interference RNA Gene Knockdown of Pancreatitis-Associated Proteins in Rat Acute Pancreatitis", *Pancreas*, 2008, 36: 402-410; (3) Kandil et al., "Dexamethasone Mediates Protection Against Acute Pancreatitis via Upregulation of Pancreatitis-Associated Proteins", *World J. Gastroenterol*, 2006, 12(42): 6806-6811; (4) Viterbo et al., "Pancreatitis-Associated Protein 2 Modulates Inflammatory Responses in Macrophages", *Journal of Immunology*, 2008, 181: 1948-1958; (5) Kandil et al., "Targeted Inhibition of Gene Expression of Pancreatitis-Associated Proteins Exacerbates the Severity of Acute Pancreatitis in Rats", *Scand J. Gastroenterol.*, 2004, 39: 870-881; and (6) Viterbo et al., "Administration of Anti-Reg I and Anti-PAPII Antibodies Worsens Pancreatitis", *J. Pancreas* (Online), 2009, 10(1): 15-23.

The table below sets forth all senuences used in the present application:

| Seq. ID | | Seq. Name |
|---|---|---|
| 1 | LVTTLKSWFQADLACQKRPSGHLVSILSGG EASFVSSLVTGRVNNNQDIWIWLHDPTMGQ QPNGGGWEWSNSDVLNYLNWDGDPSSTV NRGNCGSLTATSEFLKWGDHHCDVELPFVC KFKQ | N-truncated PAP2 (28-149) |
| 2 | EDSQKAVPSTRTSCPMGSKAYRSYCYTLVT TLKSWFQADLACQKRPSGHLVSILSGGEAS FVSSLVTGRVNNNQDIWIWLHDPTMGQQP NGGGWEWSNSDVLNYLNWDGDPSSTVNR GN | C-truncation PAP2 (1-119) |
| 3 | GTAACTCTGACGTACTGAATTATC | Cysteine 42 Primer Forwar |
| 4 | CTTAGTGGAGGTGAGGCTTCCTT | Cysteine 42 Primer Reverse |
| 5 | TATCTCAACTGGGATGGGGATCC | Cysteine 120 Primer Forward |
| 6 | TTCCTCTACTGTCAACCGTGGTAACTG | Cysteine 120 Primer Reverse |
| 7 | GGAGACCATCACTCTGATGTGGAATTACC | Cysteine 137 Primer Forward |
| 8 | GGTAATTCCACATCAGAGTGATGGTCTCC | Cysteine 137 Primer Reverse |
| 9 | GGAATTACCTTTTGTCTCCAAGTTCAAGC AGTA | Cysteine 145 Primer Forward |
| 10 | TACTGCTTGAACTTGGAGACAAAAGGTAA TTCC | Cysteine 145 Prime Reverse |
| 11 | AGCCCATGATTTAGAGACCAT | Real-Time PCR IL-1α Forward Primer |
| 12 | TGATGAACTCCTGCTTGACGAT | Real-Time PCR IL-1α Reverse Primer |
| 13 | CAGATCAGCACCTCACAGCTTCCAGAATA ATT | Real-Time PCR IL-1α Probe |
| 14 | CCAAGCACCTTCTTTTCCTTCA | Real-Time PCR IL-1β Forward Primer |
| 15 | AGCCTGCAGTGCAGCTGTCTAA | Real-Time PCR IL-1β Reverse Primer |
| 16 | AGCCCGTCCTCTGTGACTCGTGGGATGA | Real-Time PCR IL-1β Probe |
| 17 | TCCAAACTGGATATAACCAGGAAAT | Real-Time PCR IL-6 Forward Primer |

-continued

| Seq. ID | | Seq. Name |
|---|---|---|
| 18 | TTGTCTTTCTTGTTATCTTGTAAGTTGTTCTT | Real-Time PCR IL-6 Reverse Primer |
| 19 | AATCTGCTCTGGTCTTCTGGAGTTCCGTTTCTA | Real-Time PCR IL-6 Probe |
| 20 | GACCCTCACACTCAGATCATCTTCT | Real-Time PCR TNFα Forward Primer |
| 21 | TTGTCTTTGAGATCCATGCCATT | Real-Time PCR TNFα Reverse Primer |
| 22 | ACGTCGTAGCAAACCACCAAGCGGA | Real-Time PCR TNFα Probe |
| 23 | agc aga att cgaagactcccagaaggcagtgccctctacacg | Forward Primer-5' |
| 24 | ctc act cga ggt cta ctg ctt gaa ctt gca gac aaa agg taa ttc cac atc | Reverse Primer-5' |
| 25 | TMGQQPNGGGWEWSNSDVLNYLNWDGDPSST | Polyclonal Rabbit Anti-rat PAP2 |
| 26 | agcagaattc gaagactcccagaaggcagtgccctctacacg | Primer EcoRI |
| 27 | ctcactcgag gtc tac tgc ttg aac ttg cag aca aaa ggt aat tcc aca tc | XhoI |
| 28 | EDSQKAVPSTRTSCPMGSKAYRSYCYTLVT TLKSWFQADLACQKRPSGHLVSILSGGEAS FVSSLVTGRVNNNQDIWIWLHDPTMGQQP NGGGWEWSNSDVLNYLNWDGDPSSTVNR GNCGSLTATSEFLKWGDHHCDVELPFVCKF KQ | Translated PAP2 Sequence |
| 29 | TMGQQPNGGGWEWSNSDVLNYLNWDGDPSST | Peptide Sequence Used to Generate anti-PAP2 Antibody |
| 30 | TMGQQPNGGGWEWSNSDVLNYLNWDGDPSS | Rat PAP2 Peptide |
| 31 | GLHDPKNNRRWHWSSGSLFLYKSWDTGYPNN | Rat Reg1 Sequence |
| 32 | GTTCCTGACTTGTTTGAAGA | Gene IL-1α Forward Primer |
| 33 | GATATCTGGAAATCTATCAT | Gene IL-1α Reverse Primer |
| 34 | TGAACTCAACTGTGAAATAG | Gene IL-β Forward Primer |
| 35 | CCATTGCTGTTTCCTAGGAA | Gene IL-β Reverse Primer |
| 36 | CCGGAGAGGAGACTTCACAG | Gene IL-6 Forward Primer |
| 37 | GAGCATTGGAAGTTGGGGTA | Gene IL-6 Reverse Primer |
| 38 | ACTGAACTTCGGGGTGATCG | Gene TNFα Forward Primer |
| 39 | GTGGTGAGGAGCACATAGT | Gene TNFα Reverse Primer |
| 40 | GGCATTGTCACCAACTGGGA | Gene B-actin Forward Primer |
| 41 | ATCGTACTCCTGCTTGCTGA | Gene B-actin Reverse Primer |

What is claimed is:

1. A truncated pancreatitis associated protein of the sequence listing (SEQ ID NO: 1)
LVTTLKSWFQADLACQKRPSGHLVSILSGGEASFVSSLVTGRVNNNQDIW

IWLHDPTMGQQPNGGGWEWSNSDVLNYLNWDGDPSSTVNRGNCGSLTATS

EFLKWGDHHCDVELPFVCKFKQ.

2. The truncated pancreatitis associated protein of claim 1, wherein said protein is in substantially purified form.

3. A peptide sequence usable to make anti-PAP2 antibody of the sequence TMGQQPNGGGWEWSNSDVLNYLNWDGDPSST (SEQ ID. NO. 25).

4. A method of treating pancreatitis, comprising:
providing a mammal having pancreatitis; and
administering a therapeutically effective amount of truncated pancreatitis associated protein of the sequence listing (SEQ ID NO: 1)
LVTTLKSWFQADLACQKRPSGHLVSILSGGEASFVSSLVTGRVNNNQDIWI

WLHDPTMGQQPNGGGWEWSNSDVLNYLNWDGDPSSTVNRGNCGSLTATSEF

LKWGDHHCDVELPFVCKFKQ.

5. The method of claim 4, further comprising the step of correlating a dose with a result.

6. The method of claim 5, wherein said result is selected from the group consisting of clinical assessment of acute abdomen, white count, and elevated amylase and lipase levels.

7. The method of claim 4, further comprising the step of observing the expression of NF-κB.

8. The method of claim 7, further wherein observing is measured by a method selected from the group consisting of ELISA, a western blot, or a PCR.

9. A method of providing an immunomodulatory effect in a mammal with pancreatitis, comprising:
administering to the mammal in need thereof a therapeutically effective amount of a truncated pancreatitis associated protein of the sequence listing (SEQ ID NO: 1)
LVTTLKSWFQADLACQKRPSGHLVSILSGGEASFVSSLVTGRVNNNQDIWI

WLHDPTMGQQPNGGGWEWSNSDVLNYLNWDGDPSSTVNRGNCGSLTATSEF

LKWGDHHCDVELPFVCKFKQ.

10. A method of making recombinant truncated pancreatitis-associated protein of the sequence listing (SEQ ID NO: 1)
LVTTLKSWFQADLACQKRPSGHLVSILSGGEASFVSSLVTGRVNNNQDIWI

WLHDPTMGQQPNGGGWEWSNSDVLNYLNWDGDPSSTVNRGNCGSLTATSEF

LKWGDHHCDVELPFVCKFKQ, comprising the steps of:
Inserting a nucleic acid encoding SEQ ID NO:1 in-frame into a pET24a bacterial expression vector;
growing a plurality of positive clones transformed into a plurality of bacterium to a density in a medium;
centrifuging and resuspending the bacterium in a resuspension buffer;
sonicating the bacterium with a protease inhibitor to lyse the cells;
centrifuging and washing the bacterial cell lysate pellet in a first buffer;
solubilizing said bacterial cell lysate pellet in a second buffer containing 6 M urea.

* * * * *